United States Patent
Fogarty et al.

(10) Patent No.: US 6,193,745 B1
(45) Date of Patent: Feb. 27, 2001

(54) MODULAR INTRALUMINAL PROSTEHESES CONSTRUCTION AND METHODS

(75) Inventors: Thomas J. Fogarty, Portola Valley; Kirsten Freislinger, Menlo Park, both of CA (US); Steven Weinberg, League City, TX (US); Brian J. Cox, Los Altos, CA (US); Michael A. Evans, Palo Alto, CA (US); Steven W. Kim, Sunnyvale, CA (US); Jay A. Lenker, Los Altos, CA (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 08/868,902

(22) Filed: Jun. 4, 1997

Related U.S. Application Data

(62) Division of application No. 08/538,706, filed on Oct. 3, 1995, now Pat. No. 5,824,037.

(51) Int. Cl.$^7$ .................................. A61F 2/04; A61F 2/06
(52) U.S. Cl. ..................... 623/1.12; 623/1.13; 623/1.36
(58) Field of Search ................................. 623/1, 11, 12, 623/1.12, 1.13, 1.36; 606/192, 194, 195, 198

(56) References Cited

U.S. PATENT DOCUMENTS

| | | | |
|---|---|---|---|
| 3,986,828 | 10/1976 | Hoffman, Jr. .................. | 8/115.5 |
| 4,580,568 | 4/1986 | Gianturco ...................... | 128/345 |
| 4,728,328 | 3/1988 | Hughes et al. ................. | 623/12 |
| 4,776,337 | 10/1988 | Palmaz ........................... | 128/343 |
| 4,872,874 | 10/1989 | Taheri ............................ | 623/1 |
| 4,892,539 | 1/1990 | Koch ............................. | 623/1 |
| 4,957,508 | 9/1990 | Kaneko et al. ................. | 623/12 |

(List continued on next page.)

FOREIGN PATENT DOCUMENTS

| | | | |
|---|---|---|---|
| 0 334 567 A2 | 3/1989 | (EP) | A61F/2/06 |
| 0 357 003 B1 | 8/1989 | (EP) | A61F/2/00 |
| 0 587 197 A1 | 10/1991 | (EP) | A61F/2/04 |
| 0 501 890 A1 | 2/1992 | (EP) | A61F/2/06 |
| 0 539 237 A1 | 10/1992 | (EP) | A61F/2/06 |
| 0 621 015 A1 | 4/1993 | (EP) | A61F/2/06 |

(List continued on next page.)

OTHER PUBLICATIONS

World Medical Manufacturing Corporation Internet WEB Page Information, downloaded Aug. 4, 1997.

*Primary Examiner*—Mickey Yu
*Assistant Examiner*—Choon P. Koh

(57) ABSTRACT

The present invention provides modular intraluminal tubular prostheses, particularly stents and stent-grafts, for the treatment of disease conditions, particularly aneurysms. Modular sections of the prostheses, or "prosthetic modules," may be selectively combined to form a composite prosthesis having characteristics which are tailored to the specific requirements of the patient. Each prosthetic module preferably includes one or more standard interface ends for engaging another module, the module/module interface typically comprising ends which overlap and/or lock within a predetermined axial range. Advantageously, the axial length, cross-section, perimeter, resilient expansive force, axial flexibility, liner permeability, liner extensibility, radial conformability, liner/tubal wall sealing and anchoring, and other prosthetic characteristics may be varied along the axis of the composite prosthesis, and also along the axis of each prosthetic module. The modules are preferably individually introduced into a lumen system of a patient body so that the composite prosthesis is assembled in situ. Ideally, selection of appropriate prosthetic modules and the flexibility of the interface overlap range provides a custom fit intraluminal prosthesis which provides a therapy tailored to the individual patient's needs.

6 Claims, 15 Drawing Sheets

U.S. PATENT DOCUMENTS

| | | | |
|---|---|---|---|
| 5,064,435 | 11/1991 | Porter | 623/12 |
| 5,122,154 | 6/1992 | Rhodes | 606/198 |
| 5,211,658 | 5/1993 | Clouse | 623/1 |
| 5,282,823 | 2/1994 | Schwartz et al. | 606/198 |
| 5,282,847 | 2/1994 | Trescony et al. | 623/1 |
| 5,316,023 | 5/1994 | Palmaz et al. | 128/898 |
| 5,330,500 | 7/1994 | Song | 606/198 |
| 5,354,308 | 10/1994 | Simon et al. | 606/198 |
| 5,366,504 | 11/1994 | Anderson et al. | 623/11 |
| 5,383,928 | 1/1995 | Scott et al. | 623/1 |
| 5,385,580 | 1/1995 | Schmitt | 623/1 |
| 5,413,598 | 5/1995 | Moreland | 623/1 |
| 5,443,496 | 8/1995 | Schwartz et al. | 623/1 |
| 5,443,497 | 8/1995 | Venbrux | 623/1 |
| 5,443,499 | 8/1995 | Schmitt | 623/1 |
| 5,456,713 | 10/1995 | Chuter | 623/1 |
| 5,507,769 | 4/1996 | Marin et al. | 606/198 |
| 5,507,771 | 4/1996 | Gianturco | 606/198 |
| 5,562,725 | 10/1996 | Schmitt et al. | 623/1 |
| 5,562,727 | 10/1996 | Turk et al. | 623/1 |
| 5,591,195 | 1/1997 | Taheri et al. | 606/194 |
| 5,617,878 | 4/1997 | Taheri | 606/898 |
| 5,618,301 | 4/1997 | Hauenstein et al. | 606/198 |
| 5,632,763 | 5/1997 | Glastra | 606/194 |
| 5,632,772 | 5/1997 | Alcime et al. | 623/1 |
| 5,662,675 | 9/1997 | Polanskyj Stockert et al. | 606/196 |
| 5,876,448 * | 3/1999 | Thompson et al. | 623/12 |

FOREIGN PATENT DOCUMENTS

| | | | |
|---|---|---|---|
| 0 666 065 A1 | 2/1994 | (EP) | A61F/2/06 |
| 0 621 016 A1 | 4/1994 | (EP) | A61F/2/06 |
| 0 546 021 B1 | 8/1994 | (EP) | A61F/2/06 |
| 0 684 022 A2 | 4/1995 | (EP) | A61F/2/06 |
| 0 689 806 A2 | 5/1995 | (EP) | A61F/2/06 |
| 0 689 805 A2 | 6/1995 | (EP) | A61F/2/06 |
| 686379 | 12/1995 | (EP) . | |
| 2 678 508 | 7/1991 | (FR) | A61F/2/06 |
| 2 714 816 | 11/1994 | (FR) | A61F/2/06 |
| WO 94/24961 | 11/1994 | (WO) | A61F/2/06 |
| WO 95/09586 | 4/1995 | (WO) | A61F/2/06 |
| WO 95/32757 | 4/1995 | (WO) | A61M/29/00 |
| WO 95/16406 | 6/1995 | (WO) | A61F/2/06 |
| WO 95/34255 | 6/1995 | (WO) | A61F/2/06 |
| WO 96/00103 | 6/1995 | (WO) | A61M/29/00 |
| WO 95/21592 | 8/1995 | (WO) . | |
| WO 95/32688 | 12/1995 | (WO) . | |
| WO 96/10967 | 4/1996 | (WO) | A61M/2/04 |
| WO 97/07751 | 3/1997 | (WO) . | |

* cited by examiner

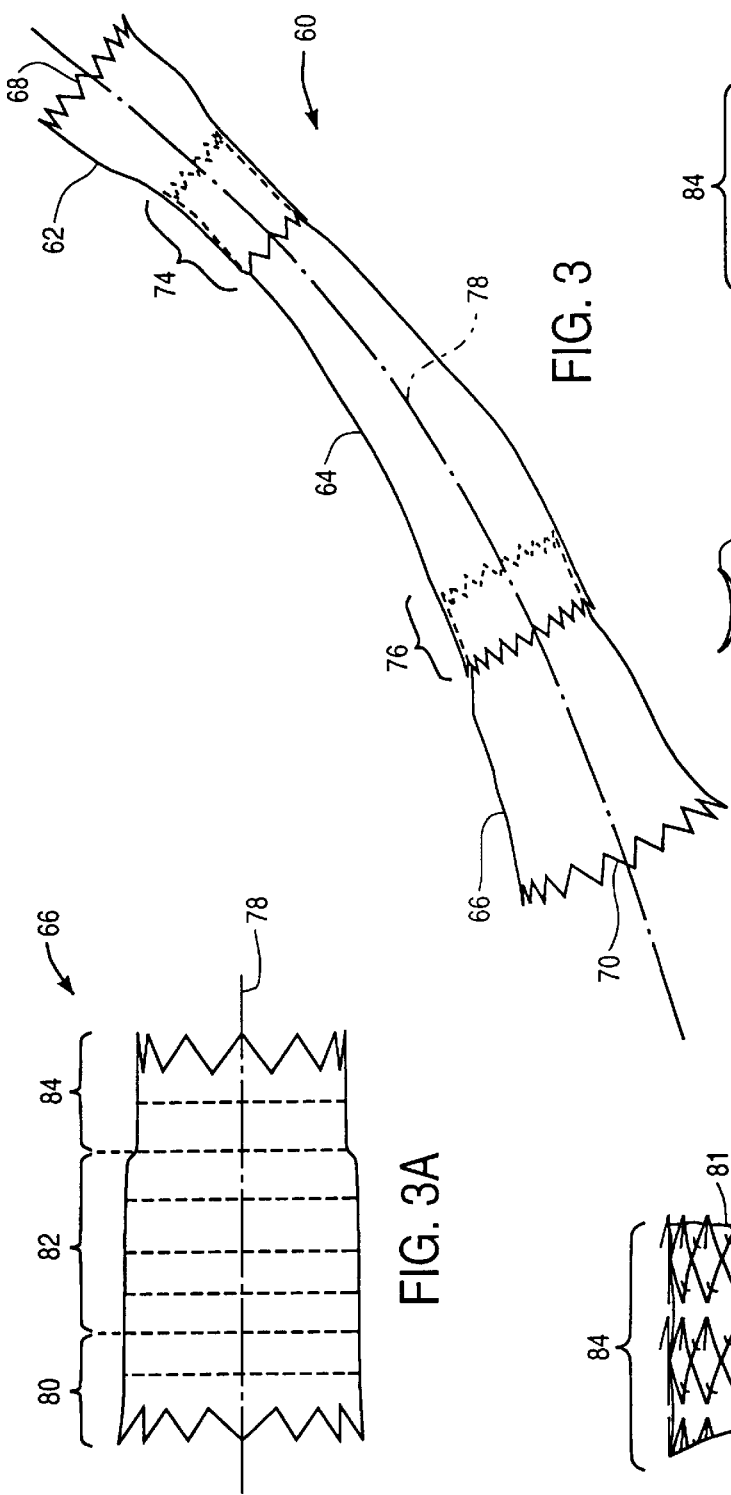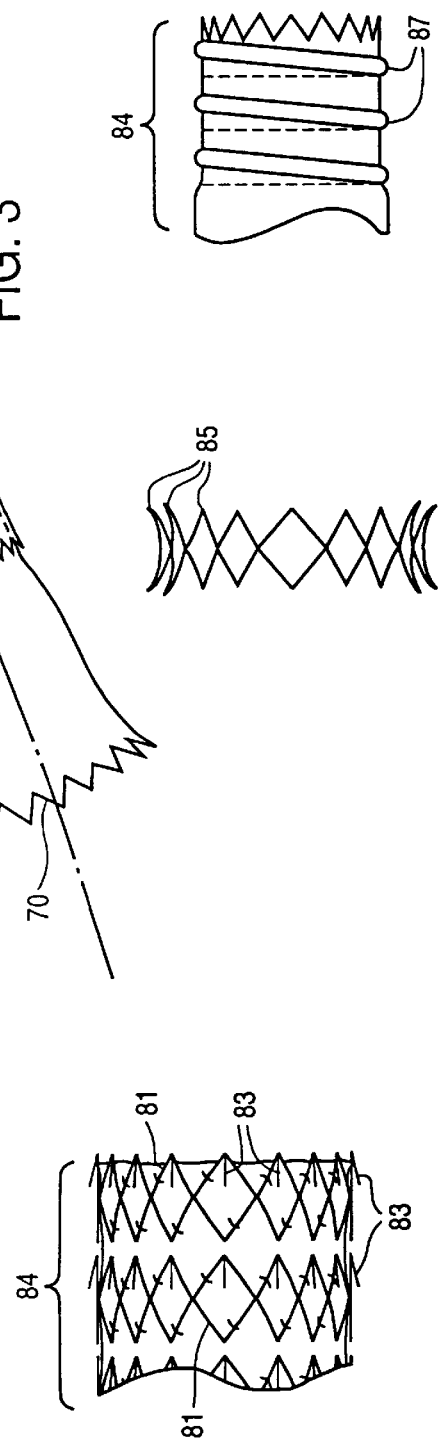

MODULAR INTRALUMINAL PROSTEHESES CONSTRUCTION AND METHODS

This is a division of application Ser. No. 08/538,706 filed Oct. 3, 1995 U.S. Pat. No. 5,824,037 the disclosure of which is incorporated by reference.

BACKGROUND OF THE INVENTION

1. Field of the Invention

The present invention relates generally to endoluminal tubular prostheses, such as stents, stent-grafts, and other structures. More particularly, the present invention provides modular tubular prosthesis structures having properties which can be tailored for individual body lumens, including blood vessels, particularly for the treatment of abdominal and other aneurysms.

Vascular aneurysms are the result of abnormal dilation of a blood vessel, usually resulting from disease and/or genetic predisposition, which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending distally into one or both of the iliac arteries.

Aortic aneurysms are most commonly treated in open surgical procedures where the diseased vessel segment is bypassed and repaired with an artificial vascular graft. While considered to be an effective surgical technique, particularly considering the alternative of a usually fatal ruptured abdominal aortic aneurysm, conventional vascular graft surgery suffers from a number of disadvantages. The surgical procedure is complex and requires experienced surgeons and well equipped surgical facilities. Even with the best surgeons and equipment, however, patients being treated frequently are elderly and weakened from cardiovascular and other diseases, reducing the number of eligible patients. Even for eligible patients prior to rupture, conventional aneurysm repair has a relatively high mortality rate, usually from 2% to 10%. Morbidity related to the conventional surgery includes myocardial infarction, renal failure, impotence, paralysis, and other conditions. Additionally, even with successful surgery, recovery takes several weeks, and often requires a lengthy hospital stay.

In order to overcome some or all of these drawbacks, endovascular prosthesis placement for the treatment of aneurysms has been proposed. Although very promising, many of the proposed methods and apparatus suffer from undesirable limitations. In particular, proper sizing of endovascular prostheses can be problematic.

Proper matching of the prosthesis to the blood vessel is critical to the treatment of an aneurysm. The prosthesis preferably extends axially beyond the weakened portion of the blood vessel to anchor securely in the healthy vessel wall. However, the cross-sectional size and axial length of individual blood vessels vary considerably between patients. Even within a patient, the cross-section and resilience of a lumen wall can vary considerably along its axial length, and the location and extent of the aneurysm will differ with different patients. Additionally, each prosthesis must be carefully constructed and handled, making it extremely costly to provide and maintain the large selection of prostheses required for proper fitting of every individual patient.

Known intraluminal prostheses may generally be characterized as either resilient, locking, or malleable structures. Resilient intraluminal prostheses are often formed as stent-grafts which radially conform to adapt to variations in lumen cross-section, and which will also accept some axial curvature. However, the stent-graft structures themselves have typically been formed with simplistic cylindrical frames or "stents" having axially constant diameters, constant expansive forces, and constant flexibilities along their lengths. A separate cylindrical liner or "graft" is typically attached to the frame to prevent blood flow through a ruptured vessel wall. Such liners are typically inelastic to prevent pressure from distending a weakened luminal wall. Unfortunately, inelastic liners can wrinkle or fold when the stent-graft is radially compressed from a fully expanded size, or when a portion of the liner is axially compressed by, for example, axially bending of the prosthesis. Such wrinkles or folds in the liner can substantially occlude the flow through the lumen of the prosthesis, or may result in leakage around the perimeter of the prosthesis.

Additionally, resilient stent-grafts must expand against the luminal wall with sufficient force to anchor the prosthesis within the body lumen, and should ideally be sealed around the perimeter of the luminal wall to prevent leakage. A cylindrical stent-graft large enough to provide such an anchor and seal against a healthy luminal wall may, in some patients, also impose an unacceptably high resilient expansive force at the aneurysm or other disease condition. Therefore, effective endoluminal prosthetic therapies require accurate fitting, even of resilient prosthesis, to the specific disease site and to the individual patient's vascular system.

On the other hand, malleable intraluminal prostheses can usually be expanded to fit the lumen when implanted, but the expanded prosthesis generally does not conform to irregular luminal cross-sections. The expanded prosthesis must be sufficiently rigid and sufficiently large to provide a stable anchor. Malleable prostheses are therefore expanded mechanically in situ, typically with a balloon catheter. The problem is that the expanded prosthesis assumes the shape of the cylindrical balloon catheter rather than the irregular shape of the body lumen. Furthermore, the entire perimeter of the prosthesis must be in contact with the luminal wall to provide sealing. Hence, the luminal wall is forced to assume a circular cross-section and is generally distended to a relatively large diameter.

For these reasons, it would be desirable to provide improved endoluminal prostheses, including stents and stent-grafts, and improved methods for placement of such endoluminal prostheses to treat aneurysms and other conditions. It would further be desirable to provide endoluminal prostheses which accept variations in geometry along body lumens without compromising their therapeutic effectiveness. It would further be desirable to provide adaptable prostheses and methods for their placement which would facilitate effective treatment of widely varying luminal system geometries without requiring an excessive inventory of prostheses to chose from.

2. Description of the Background Art

U.S. Pat. No. 5,064,435 describes a self expanding prosthesis which maintains a stable axial length during expansion by anchoring of radially outward flares at each end, and by sliding of an overlapping medial region therebetween.

Vascular grafts and devices for their endoluminal placement are described in U.S. Pat. Nos. 5,282,824; 5,272,971; 5,242,399; 5,219,355; 5,211,658; 5,201,757; 5,192,297; 5,190,058; 5,158,548; 5,147,370; 5,104,399; 5,092,877; 5,078,726; 5,019,085; 4,990,151; 4,950,227; 4,913,141; 4,886,062; 4,820,298; 4,787,899; 4,617,932; 4,562,596; 4,577,631; and 4,140,126; and European Patent Publications 539,237; 533,511; 518,839; 518,704; 508 473; 505,686; 466 518; and 461 791. Catheters for placing vascular stents are described in U.S. Pat. Nos. 5,192,297; 5,092,877; 5,089,005; 5,037,427; 4,969,890; and 4,886,062. Catheters carding a graft structure in a tube or capsule are described in U.S. Pat. Nos. 5,275,622; 5,104,399; and 4,787,899; and EP466518.

SUMMARY OF THE INVENTION

The present invention provides modular intraluminal tubular prostheses, particularly stents and stent-grafts, for the treatment of disease conditions, particularly aneurysms. Modular sections of the prostheses, or "prosthetic modules," may be selectively combined to form a composite prosthesis having characteristics which are tailored to the specific requirements of the patient. Each prosthetic module preferably includes one or more standard interface ends for engaging another module, the module/module interface typically comprising ends which overlap and/or lock within a predetermined axial range. Advantageously, the axial length, cross-section, perimeter, resilient expansive force, axial flexibility, liner permeability, liner extensibility, radial conformability, liner/tubal wall sealing and anchoring, and other prosthetic characteristics may be varied along the axis of the composite prosthesis, and also along the axis of each prosthetic module. The modules are preferably individually introduced into a lumen system of a patient body so that the composite prosthesis is assembled in situ. Ideally, selection of appropriate prosthetic modules and the flexibility of the interface overlap range provides a custom fit intraluminal prosthesis which provides a therapy tailored to the individual patient's needs.

In contrast with the endoluminal prostheses of the prior art, which have typically comprised either cylindrical resiliently expansive structures or malleable structures which expand to rigid circular shapes, the prostheses of the present invention preferably include extensible, flexible liners which can be selectively and plastically expanded to match the perimeter of an irregular body lumen. This expansible liner is particularly advantageous when combined with a resilient frame in a "liner-limited" stent-graft, as the resilient frame will conform to the luminal wall after the balloon catheter (or other expansion device) is removed. Moreover, as the frame is radially restrained by the expanded liner rather than the luminal wall alone, the frame will maintain both a radially taut liner surface and a limited contact force between the resilient stent-graft and the perimeter of an irregular inner surface of the luminal wall. Finally, selective axial expansion of the stent-graft eliminates any unnecessary expansive force at the aneurysm itself, as the adjacent liner maintains its unexpanded perimeter.

The intraluminal prostheses of the present invention are suitable for a wide variety of therapeutic uses, including stenting of the ureter, urethra, biliary tract, and the like. The present devices and methods will also be useful for the creation of temporary or long term lumens, such as the formation of fistulas. The present invention will find its greatest use, however, in the placement of endovascular prostheses into blood vessels for the treatment of abdominal and other aneurysms, vascular stenoses, and the like.

In a first aspect, the present invention provides a endoluminal prosthesis kit comprising a first radially expandable prosthetic module and a plurality of alternative second radially expandable prosthetic modules. The first module includes a body portion and a first interface end. Each of the second modules also has a body portion, and each includes a second standard interface end. Each of the second interface ends is fittingly engageable with the first interface end while the different body portions of the alternative second modules provide different selectable prosthetic characteristics.

Generally, the alternative body portions will differ in length, cross-section, taper, bend angle, axial flexibility, interior fiber protrusion, liner permeability, liner extensibility, radial conformability, or resilient radial spring force. In a particularly preferred embodiment, the first and second interface ends overlap within a predetermined range when engaged. This overlap range allows the total axial length of the composite prosthesis to be tailored to the particular patient's needs. Oftentimes, the present kit will further comprise a plurality of alternative third prosthetic modules, each again having a standard interface for engaging at least one of the second prosthetic modules opposite the first prosthetic module.

In another aspect, the present invention provides an endoluminal prosthetic module having a radially compressible tubular body and at least one standard interface end which is fittingly engageable with any of a plurality of other standard interface ends. Preferably, the standard interface is adapted for engagement, i.e. the interface end being axially stiff to engage the other interface end without folding or bending, and/or having radially protruding barbs to pierce an engaged interface liner portion of the other standard interface end, thereby providing a positive, locked coupling. Ideally, at least an outer interface end comprises an inexpansible liner material, which prevents distending the body lumen at the coupling, even while plastically expanding an inner interface end.

In a still further aspect, the present invention provides an endoluminal prosthesis comprising a first prosthetic module having a radially compressible tubular body, a first expansile cuff adapted to radially seal against a surrounding body lumen, and a first standard interface end. A second prosthetic module has a second radially compressible tubular body and second standard interface end which fittingly engages the first standard interface end. Typically, the engagement between the first and second interface ends prevents both axial and radial movement of the interface ends relative to each other. Once again, an overlap within a predetermined range provides flexibility in the total axial length of the composite prosthesis of the present invention.

In yet another aspect, the present invention provides a liner-limited stent-graft comprising a resilient radially expandable tubular frame, and a tubular liner disposed over at least a portion of an inner or outer surface of the frame. The liner limits the resilient expansion of at least a portion of the frame when the stent-graft is in a relaxed state. Advantageously, when the liner is disposed within the frame the tension from the frame provides a smooth prosthetic lumen defined at least in part by a taut liner surface. Furthermore, axial variations in the perimeter of the liner produce axial variations in the stent-graft lumen, even where the frame structure remains axially uniform in diameter. Such liner-limited stent-grafts are particularly well-suited for use with the selective shrinking or plastic expansion of a liner to produce axially tailored endoluminar prosthesis, as described hereinbelow.

In yet another aspect, the present invention provides an expansible liner stent-graft comprising a resilient radially expandable tubular frame, and a plastically expansible liner disposed over at least a portion of an inner or outer surface of the frame. Typically, the frame will impose a resilient expansive force on the liner which is less than a yield strength of the liner. Thus, when the stent-graft is in a relaxed state the frame induces some stress in the liner. Preferably, the liner is plastically expansible using a balloon catheter or other expansive device. Advantageously, such a liner can be selectively expanded at one or more axial locations without resiliently returning to its original size, preferably remaining under tension from the frame even after expansion. The frame thus keeps the expanded liner in a taut open configuration, which is particularly advantageous when the liner has been expanded in situ to match the perimeter of a surrounding body lumen.

A particularly advantageous material for forming the liner of the present expansible liner stent-graft comprises, at least in part, a partially oriented yarn. Typically, the partially oriented yarn is predominantly circumferentially oriented to promote radial expansion of the liner without changing the axial length. Preferably, any liner comprises a semipermeable membrane or textile which allows for tissue ingrowth into the liner, but which does not allow hyperplastic ingrowth through the liner and into the prosthetic lumen.

In yet another aspect, the present invention provides a stent-graft comprising a radially expandable tubular frame and a tubular liner over at least a portion of the inner or outer surface of the frame, the liner including a reduced portion which has been selectively shrunk relative to another portion. The liner may optionally be shrunk without a mandrel, or may alternatively have been shrunk over a mandrel with a shape selected to impose a particular shape or diameter on the assembled stent-graft. Methods for shrinking the liner are also provided, typically allowing shrinkage of up to 7% using heat, up to 18% using a chemical bath, and up to 20% using a combination of both.

In yet another aspect, the present invention provides a cuffed endoluminal prosthesis comprising a radially expandable tubular body portion having a proximal end, a distal end, and a lumen therebetween. An expansile cuff is disposed on at least one of the proximal and distal ends, the cuff expandable to sealingly engage a luminal wall having an inner perimeter greater than an outer perimeter of the expanded body portion. Optionally, the cuff is radially forced or flared outward relative to the body portion to provide sealing. As used herein, the term "flared" includes any local increase in perimeter, and specifically encompasses both axial tapers and steps. Alternatively, the cuff and the body expand resiliently, the cuff having a higher expansive spring force than the body to conform the luminal wall to the cuff. In a still further alternative, the cuff is more radially conformable than the body portion. As used herein, "radially conformable" means the ability for each individual segment of a tubular body to continue to expand radially when an adjoining segment of the tubular body is radially restrained. A highly radially conformable body will therefore expand until its entire perimeter is restrained by a surrounding luminal wall, despite the irregular shape of the luminal cross-section. Note that radial conformability and radially expansive spring force are independent quantities. Conformability is a measurement of the ability to fill an irregular space. In contrast, spring force is a measure of the force imposed on a restraining body.

In yet another aspect, the present invention provides a controlled flexibility stent-graft. In connection with the present invention, it has been discovered that the liner-frame attachment mechanism can have a profound effect on the flexibility of a stent-graft, particularly where independent frame elements are separately attached to the liner. The controlled flexibility stent-graft of the present invention therefore comprises a tubular liner defining an axis, and a plurality of radially expandable ring frames supporting the liner. At least some of the ring frames have a first inner frame attachment mechanism, while at least some of the ring frames have a second inner frame attachment mechanism. The second inner frame attachment mechanism provides greater relative movement between adjacent ring frames than the first attachment mechanism. Thus the flexibility of the stent-graft varies with the locations of the first and second attachment mechanisms. Optionally, the first and second attachment mechanisms comprise a sliding stitch pattern and a locked stitch pattern respectively.

In yet another aspect, the present invention provides an axially flexible endoluminal prosthesis comprising first and second radially expandable ring frames, the second ring frame having walls defining a plurality of axially oriented slots. Attachment structures pass through the slots and slidingly couple the first ring frame to the second ring frame. Typically, the attachment structures comprise stitches which also pass through a tubular liner which is coaxial with the first and second ring frames. The axial flexibility of the prosthesis is therefore defined at least in part by the axial length of the slots, and by the axial spacing between the slots. Note that the slots do not necessarily have to be parallel to the luminal access. As long as they extend from a first axial position to a second axial position they are "axially oriented" as that term is used herein.

In yet another aspect, the present invention provides a riveted stent-graft comprising a liner and a radially expandable tubular frame having a plurality of attachment holes. A plurality of rivets extend through the attachment holes and bond the frame to the liner.

In yet another aspect, the present invention provides a powdercoat polymer bonded stent-graft comprising a liner, a radially expandable tubular frame, and a powdercoat material applied to at least a portion of the frame and bonded to the liner. Preferably, the powdercoat polymer material is initially partially cured to the frame, and is then fully cured to encompass the adjacent liner.

In yet another aspect, the present invention provides a kink-resistant prosthesis comprising a tubular braid, an elastomeric material encompassing the braid and forming a sealed tube, and a plurality of radially expandable ring frames attached to the sealed tube.

In yet another aspect, the present invention provides a variable spring force prosthesis comprising a tubular liner which defines an axis, a first radially expandable ring frame having a first radial spring force, and a second radially expandable ring frame having a second radial spring force which is greater than the first radial spring force.

The present invention further provides a method for placement of modular endoluminal prosthesis comprising introducing a first prosthetic module to a body lumen and radially expanding the first module at a target location. A preferred second prosthetic module is selected from a plurality of alternative second prosthetic modules, and is introduced to the body lumen and radially expanded, the expanded preferred second prosthetic module engaging the expanded first prosthetic module. Preferably, a second standard interface end of the preferred second prosthetic module overlaps a first standard interface end of the first prosthetic module within a predetermined range to define a total prosthetic length. Ideally, the overlapping is performed within the body lumen. Alternatively, the modules may be assembled prior to introduction of the first module into the patient body, typically overlapping the modules based on fluoroscopy, ultrasound, or other imaging data.

In another aspect, the present invention provides a method for placing an endoluminal liner-limited stent-graft, the method comprising introducing the stent-graft to a target location within a body lumen, and radially expanding the stent-graft at the target location by releasing the stent-graft. The radial expansion of at least a portion of the frame is restrained by a liner attached to the frame. Advantageously, a second axial location of the frame can define a smaller perimeter than a first axial location of the frame. Optionally, the perimeter of the first axial location may be plastically expanded, thereby allowing the cross-section of the stent-graft to be selectively tailored along its axial length.

In another aspect, the present invention provides a stent-graft placement method comprising introducing a stent-graft to a target location within a body lumen, and radially expanding the stent-graft at the target location by releasing the stent-graft. A selected portion of a liner attached to the frame is plastically expanded to match the perimeter of the stent-graft with the target location. Ideally, radial expansion of at least an associated portion of the frame is restrained by the portion of the liner, both before and after the liner is plastically expanded. In a particularly advantageous embodiment, the liner is plastically expanded in situ, and the expanded stent-graft resiliently conforms with a luminal wall after expansion is complete.

BRIEF DESCRIPTION OF THE DRAWINGS

FIG. 3 illustrates a composite intraluminal prosthesis assembled from prosthetic modules according to the principles of the present invention.

FIG. 3A illustrates an individual prosthetic module having a standard interface end, as used to assemble the composite intraluminal prosthesis of FIG. 3.

FIGS. 3B and 3C illustrate ring frames having barbs for engaging the standard interface end of FIG. 3A.

FIG. 3D illustrates a helical element for sealing the standard interface end of the FIG. 3A.

DESCRIPTION OF THE SPECIFIC EMBODIMENTS

The present invention will find its greatest use as an endovascular prostheses for the treatment of diseases of the vasculature, particularly aneurysms, stenoses, and the like. The prostheses will generally be radially expandable from a narrow-diameter configuration to facilitate introduction into the body lumen, typically during surgical cutdown or percutaneous introduction procedures. Exemplary delivery catheters and methods for placement of the prostheses of the present invention are more fully described in copending U.S. patent application Ser. No. 08/475,200, the full disclosure of which is incorporated herein by reference.

Figure 1:
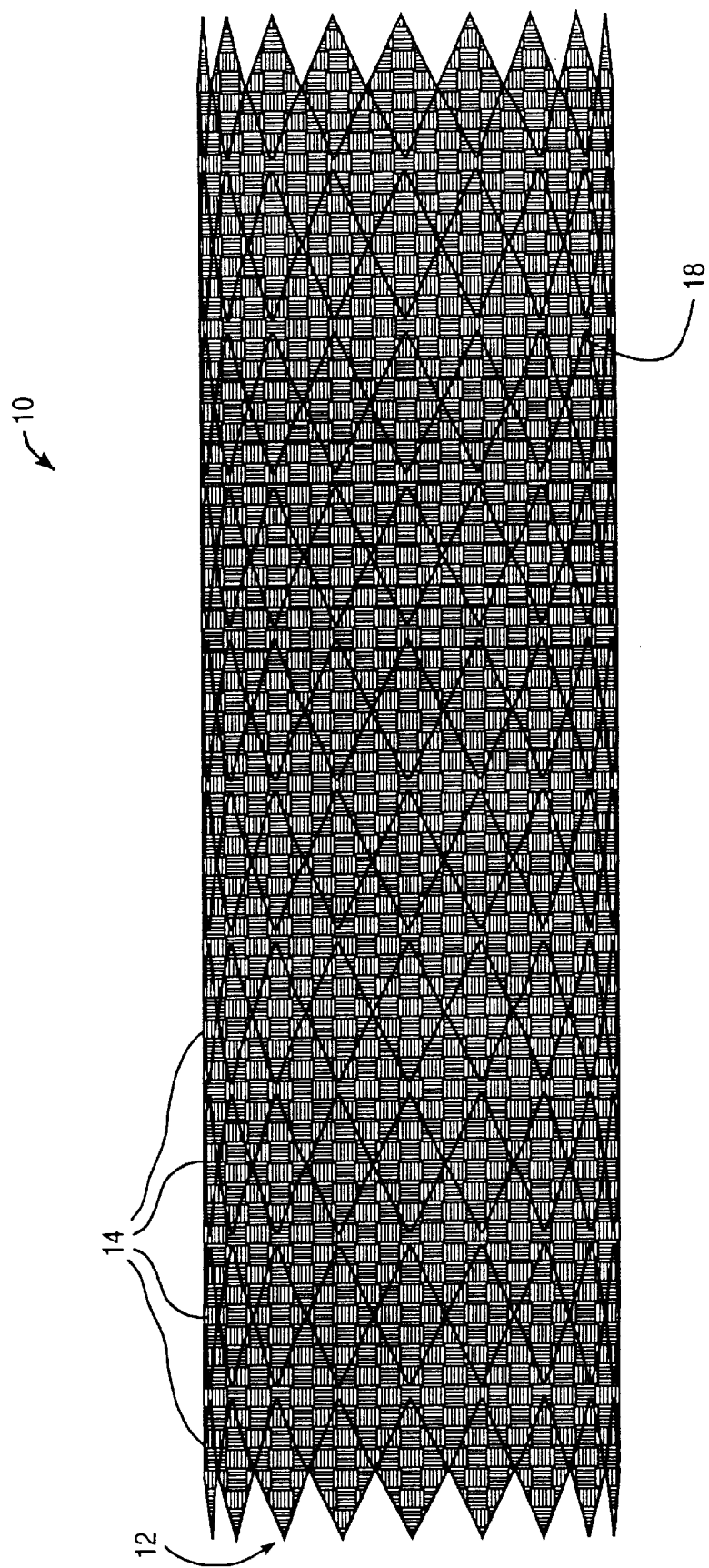
FIG. 1 is a side view of an exemplary cylindrical vascular graft having axially constant characteristics.

An exemplary cylindrical graft structure 10 is illustrated in FIG. 1. Prosthesis 10 comprises a perforate tubular frame 12 which includes a plurality of independent (non-connected) ring frames 14. The tubular frame 12 supports an inner liner 18. Optionally, an outer liner is disposed over the ring frames, either instead of inner liner 18, or in combination therewith.

To secure ring frames 14 in place, and to secure the liner to the perforate tubular frame 12, the liner is typically sutured to the frame. A wide variety of alternative liner/frame attachment mechanisms are available, including adhesive bonding, heat welding, ultrasonic welding, and the like. Where inner and outer liners are used, the ring frames may be sandwiched between the liners and held in place by attaching the liners to each other.

Although the structures and methods of the present invention will generally be described with reference to simple tubular prostheses having a single lumen, it will be understood that the structures and methods of the present invention also encompass more complex branching endoluminal prostheses.

The prosthesis 10 will typically have a length in the range from about 20 mm to 500 mm, preferably from 50 mm to 200 mm, with a relaxed diameter in the range from about 4 mm to 45 mm, preferably being in the range from 5 mm to 38 mm.

Figure 2:
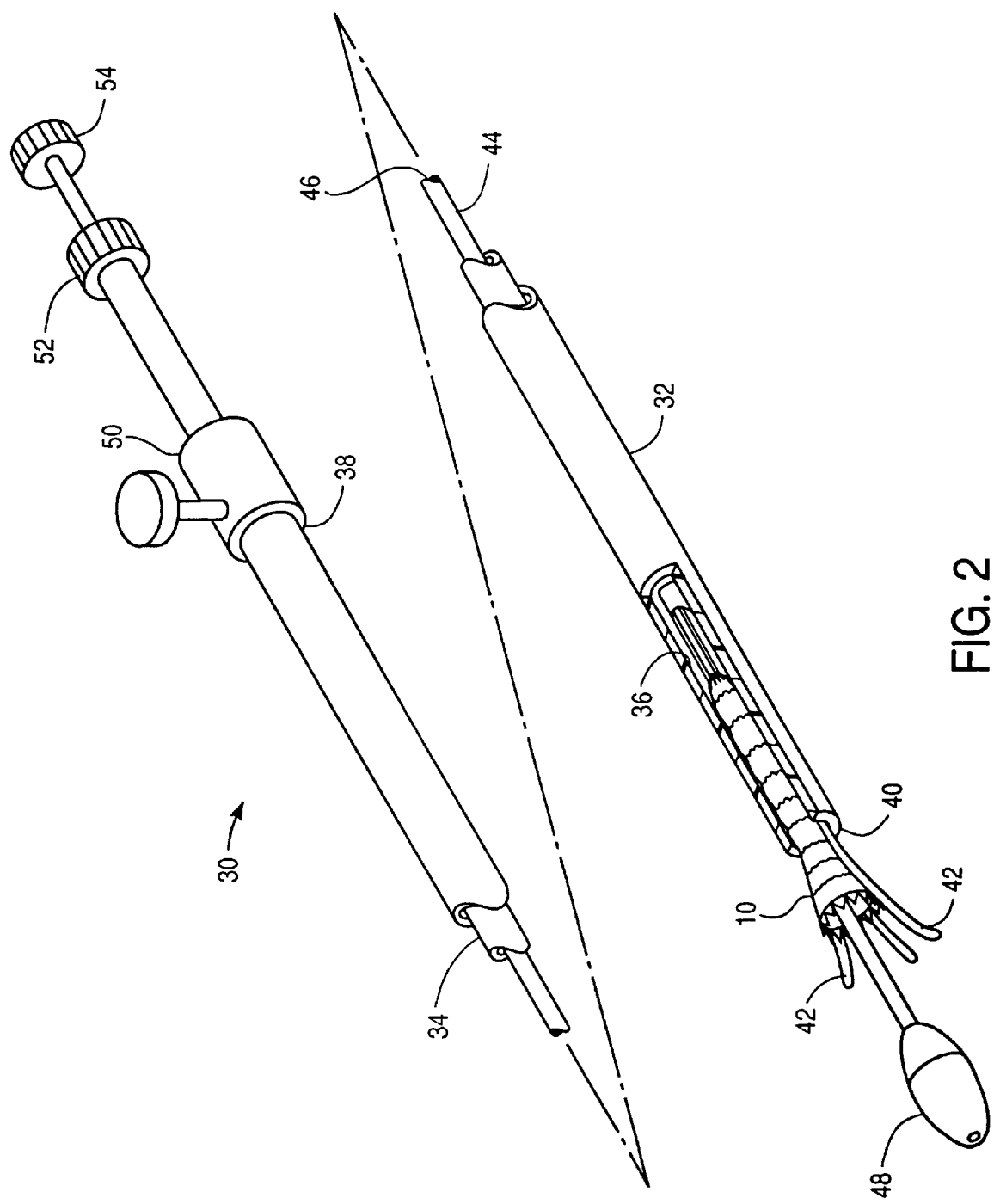
FIG. 2 is a perspective view of an exemplary delivery catheter for use with the prostheses of the present invention, with a portion of the distal end broken away to disclose a prosthesis therein.

Referring now to FIG. 2, an exemplary delivery catheter 30 for use with the endoluminal prostheses of the present invention comprises a tubular cover 32 and a shaft 34. Cover 32 has a central lumen 36 extending from a proximal end 38 to a distal end 40. Shaft 34 is slidably received within central lumen 36 and extends proximally of cover 32.

A plurality of runners 42 extend distally from shaft 34. Runners 42 line a portion of the inner surface of lumen 36, and slide within the lumen with the shaft. Shaft 34 also has a lumen, in which a core shaft 44 is slidably disposed. Core shaft 44 has a guide wire lumen 46. Nosecone 48 is fixed to the distal end of core shaft 44, and can therefore be manipulated independently of runners 42.

Prosthesis 10 is radially compressed and restrained within the plurality of runners 42. In turn, cover 32 prevents runners 42 from expanding outward. Runners 42 are formed from a hard material, and distribute the expansion load of prosthesis 10 over the inner surface of central lumen 36. The deploying force is applied proximally against a slider 50 attached to distal end 38 of cover 30, while holding a luer fitting 52 at the distal end of shaft 34, thereby withdrawing the cover proximally from over the prosthesis. An additional luer adaptor 54 at the distal end of core shaft 44 allows the core shaft to be manipulated independently, and to be releasably secured to the shaft 34.

Modular Prostheses

Referring now to FIG. 3, a composite endoluminal prostheses 60 comprises a distal cuff module 62, a tapered prosthetic module 64, and a proximal cuff module 66. Distal end 68 and proximal end 70 of composite prostheses 60 include outward flared cuffs to ensure sealing between the prostheses and the body lumen. The cross-section of composite prosthesis 60 varies axially, particularly along tapered prosthetic module 64. Composite prosthesis 60 also bends axially, again primarily about tapered prosthetic module 64, to adapt to curving body lumens.

As seen FIG. 3A, proximal cuff module 66 includes three distinct axial regions. Proximal sealing region 80 seals against a surrounding body lumen wall, as described in more detail hereinbelow. In contrast, body region 82 need not conform completely to the luminal cross-section, but typically includes relatively stiff resiliently expanding frames which firmly anchor the proximal end of composite prosthesis 60 in position. Prostheses having cuffs and ends adapted for sealing and/or anchoring are described below and in copending U.S. patent application Ser. No. 08/538,706, the full disclosure of which is incorporated herein by reference.

The third region of proximal cuff 66, interface end 84, is generally somewhat smaller in diameter than the remainder of the prosthetic module, typically being limited in size by an inelastic liner, as described in more detail hereinbelow. The inner and outer surface of the liner material of interface end 84 preferably provide a high friction connection when inserted within, or disposed over, a similar interface end. Thus, the liner-limited cross-section allows the concentric interface ends to firmly engage each other without distending the body lumen wall in the region of a distal coupling 74 or a proximal coupling 76. Ideally, the frames within interface end 84 are attached to the liner so that axial flexibility of the interface end is minimal, thereby assuring a flow path which is unobstructed by folds when two interface ends are engaged.

Referring now to FIGS. 3B and 3C, the interface end optionally includes barbs which lock the relative positions of the prosthetic modules at the couplings. Barbed ring frames 81 comprise radially protruding barbs 83 extending from the axial corners of the linked shapes. The barbs are generally axially oriented in one or both axial directions, and may-be formed when the frame ring is fabricated. Preferably, the barbs are provided on the outer surface of the inner interface end and pierce a surrounding liner of the outer interface end when engaged. Ideally, the outer liner is a textile to prevent tearing. The barbs may alternatively be formed as simple outward biased corners 85 of the ring frame which are sufficiently sharp and protruding to pierce the surrounding liner. The barbs may be mechanically bent outward, or the ring frame may be heat-treated so as to bias the barbs outward. Clearly, the liner attachment mechanism should not prevent radial protrusion of the barbs. Similar inward oriented barbs might instead be used on the outer interface end.

FIG. 3D illustrates a helical winding 87 which may help to seal the coupling, and may allow "threaded" attachment of prosthetic modules. The winding may comprise an elastomer, or may in part slide helically during radial expansion.

Figure 4:
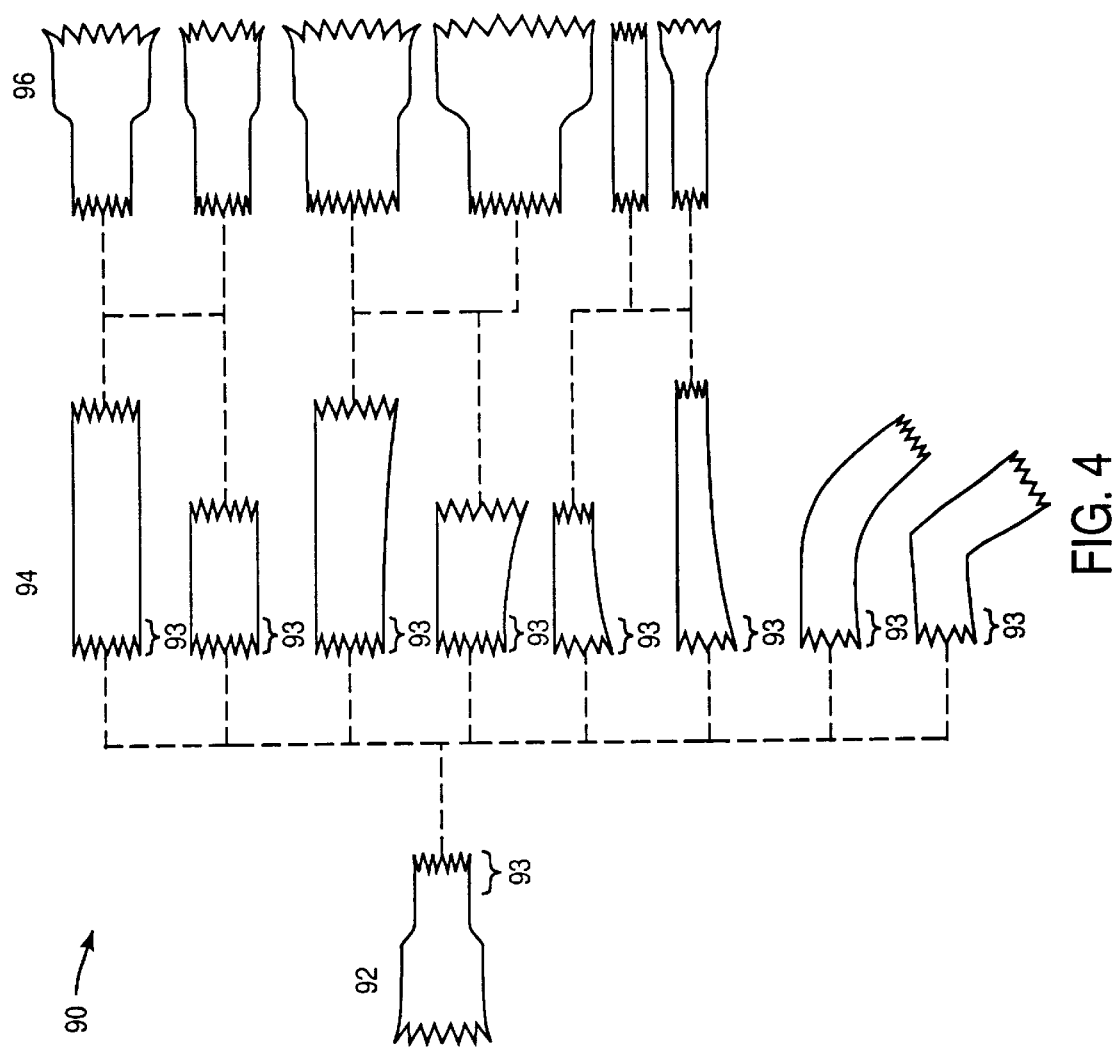
FIG. 4 is a schematic illustration of a composite prosthesis kit according to the principles of the present invention.

Referring now to FIG. 4, a composite luminal prosthesis kit 90 includes a first sealing prosthetic module 92 having a first standard interface end 93. First interface end 93 is sized to fit any of a plurality of prosthetic body modules 94. Generally, prosthetic body modules 94 have a variety of selectable body lengths, bends and taper characteristics, and each also includes a standard end 93 for engaging standard end 93 of sealing prosthetic module 92. Ideally, the interface ends are interchangeable, but they may alternatively comprise distinct inner and outer mating pairs. In a particularly preferred embodiment, multiple prosthetic body modules 94 may be directly coupled together to form a single composite prosthesis.

Prosthetic body modules 94 may further offer a variety of prosthetic characteristics, including length, cross-section, axial bend angle, axial flexibility, resilient spring force, exterior fiber protrusion, conformability, radial/axial expansive coupling, yield strength, and the like. Several of these characteristics will be described in more detail hereinbelow. Depending on the prosthetic body module selected, a variety of second sealing prosthetic modules 96 may be employed to form a complete composite prosthesis. Alternatively, an end of prosthetic body module 94 opposite interface end 93 may incorporate its own sealing cuff.

Figure 5A:
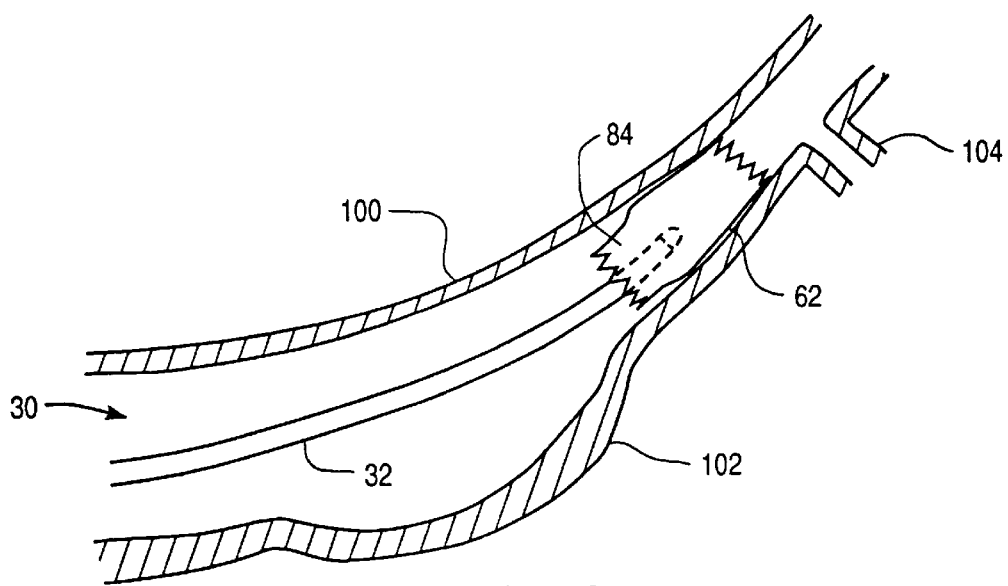
FIGS. 5A–C illustrate the deployment of multiple prosthetic modules to assemble the composite prosthetic module of FIG. 3 in situ.
Figure 5B:
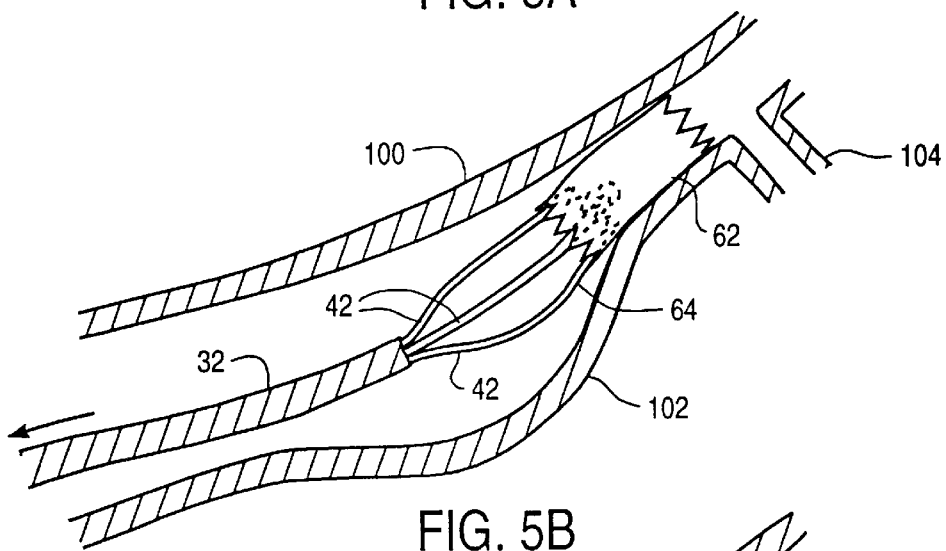

Placement and assembly of composite prosthesis 60 will be described with reference to FIGS. 5A–5C. Composite prosthesis 60 will be implanted within a blood vessel 100 having an aneurysm 102. The use of a standard cylindrical prosthesis is complicated by the presence of a branching vessel 104 in the vicinity of aneurysm 102, and by a bend and tapered shape to blood vessel 100.

Distal cuff module 62 is first positioned proximally of branch 104, but within the healthy vessel wall distal of aneurysm 102, preferably using delivery catheter 30 as seen in FIG. 2. Once the distal cuff module 62 has been positioned, another delivery catheter 30 is positioned within the body lumen extending into the standard interface end 84 of distal cuff module 62. Cover 32 is withdrawn proximally to release the tapered prosthetic module, which expands radially between runners 42 to engage the distal cuff module, thereby forming distal coupling 74. Tapered prosthetic module 64 approximates the smooth tapering shape of body lumen 100, and flexes axially without kinking or excessive wrinkling. Proximal cuff module 66 may then be introduced into another standard interface end of tapering prosthetic module 64 to form a proximal coupling 76.

Figure 5C:
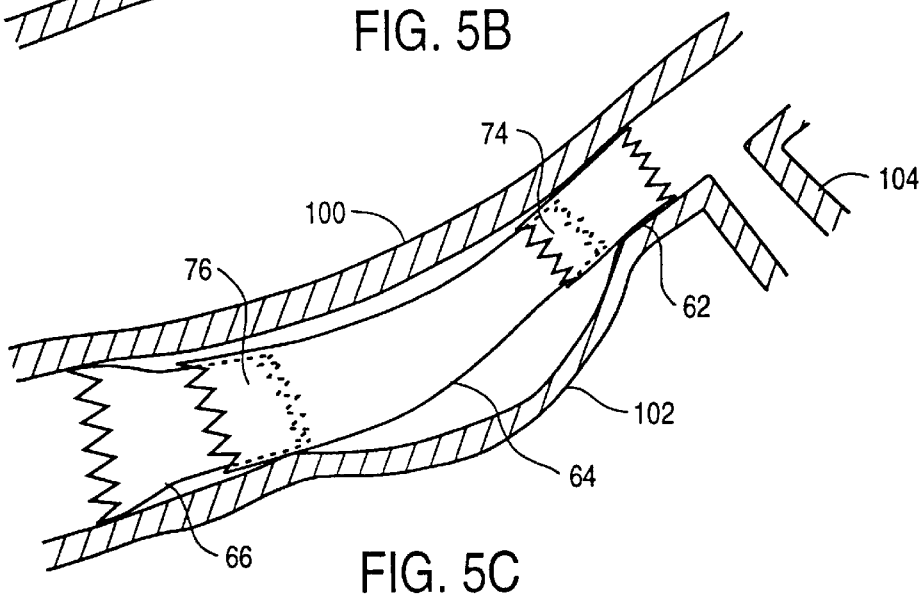

As seen in FIG. 5C, the complete composite prosthesis is effectively sealed at the proximal and distal ends by proximal and distal cuff modules 62 and 66. The various properties of the composite prosthetic module are determined by the prosthetic modules selected. The total length of the composite prosthesis is controlled by the selection of prosthetic modules, and by assembling the prosthetic modules in situ with the appropriate amount of overlap at distal and proximal couplings 74, 76.

Alternatively, the composite prosthesis may be assembled from a plurality of prosthetic modules externally, and deployed as a unit within the body lumen. Such a method allows tailoring of the size and characteristics of the composite prosthesis based on fluoroscopy, ultrasound, or other imaging modalities, but would not provide the precise fit of in situ assembly.

In a still further alternative, a single delivery catheter could be used to deploy each of the prosthetic modules, either by inserting each prosthetic module within the proximal end of the cover and advancing the modules distally using a shaft, or by preselecting the prosthetic modules and inserting them in the distal end of the delivery catheter in the reverse order of their deployment.

Cross-Sectional Variation and Control

Figure 6A:
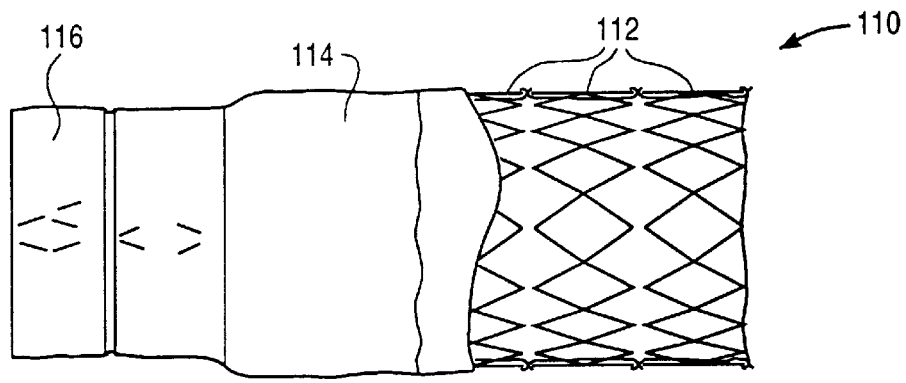
FIGS. 6A–C illustrates stent-grafts having liners which restrain the expansion of at least a portion of a resilient frame to axially vary the prostheses' cross-section according to the principles of the present invention, each stent graft having a portion of the outermost structure removed for clarity.
Figure 6B:
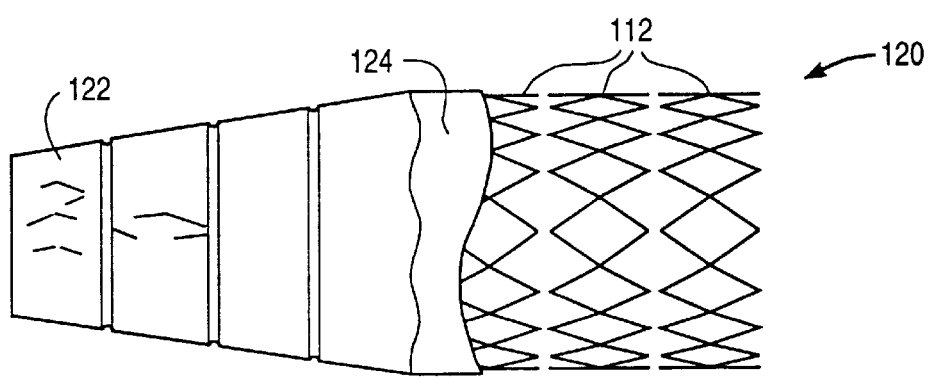
Figure 6C:
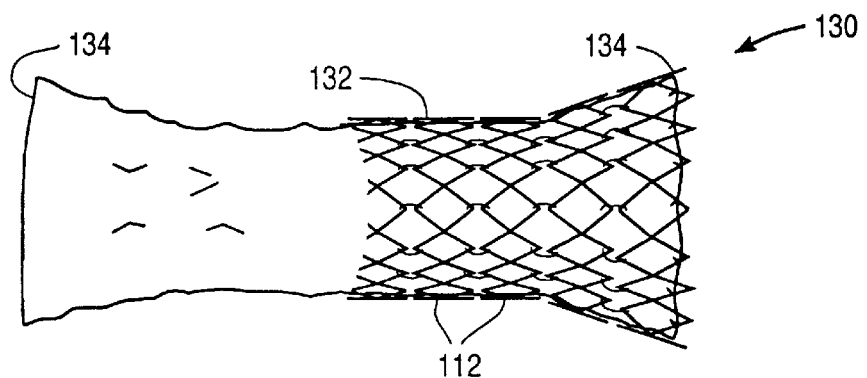

Referring now to FIGS. 6A–6C, axially varying stent-grafts 110, 120, and 130 are generally radially compressible tubular structures which vary axially in cross-section. Each prosthesis comprises a frame or "stent," formed of independent rings which are held in position by a liner. Frame rings 112 comprise linked diamond-shaped elements which are attached to an inelastic liner or "graft." Specifically, frame rings 112 may be stitched to, mechanically fastened on, adhesively bonded to, or woven into the graft material, or may alternatively be sandwiched in between inner and outer layers of graft material as described above regarding claim 1.

A first axially varying prosthesis 110 includes a plurality of frame rings 112 disposed between inner and outer layers of an inelastic sandwich graft 114 having a reduced diameter end 116. The resilient expansion of the frame rings 112 in the area of reduced diameter end 116 produces a taut outer portion of inelastic sandwich graft 114, limiting outward expansion of the stent which might otherwise stress a body lumen. Reduced diameter end 116 is therefore particularly useful as a standard interface end for coupling of prosthetic modules, as the liner prevents the combined expansive forces of the overlapping frames from distending the lumen wall.

A second axially varying prosthesis 120 includes an inelastic outer tapered graft 124 having a tapered end 122, and is particularly well suited for use in tapering body lumens.

A third axially varying prosthesis 130 includes an inelastic inner flared graft 132 which restrains the total diameter of the prosthesis from within the stent through the stent/graft attachment threads. The graft includes a greater perimeter at both ends, allowing the stent rings located in the end portions to expand to a larger diameter. The shape of this prosthesis is particularly well suited for treatment of aneurysms and other weakened vessels, as the flared ends provide secure proximal and distal anchors beyond the aneurysm, while the liner limits expansion of a central portion of the prosthesis to avoid distressing the weakened vessel wall at the aneurysm itself.

Graft material is typically highly flexible so that the prosthesis is radially compressible to a narrow diameter configuration for insertion and positioning within a body lumen. However, the graft material is also generally inelastic to avoid any stretching of the liner material after deployment, as excess loose fabric may interfere with the flow through the prosthesis lumen. As seen in each of FIGS. 6A–C, the inelastic liner of the present invention preferably limits the maximum expansion of at least a portion of the resilient frame. Specifically, at least one resilient stent ring 112 in each of axially varying prostheses 110, 120, and 130, does not reach a fully-expanded, relaxed state. Instead, the liner restrains the total expanded diameter of the prosthesis selectively along its axial length. The liner is therefore stressed by the frame, presenting a taut, smooth surface, thereby improving flow through the lumen.

Note that frame rings 112 can, but need not, comprise uniform structural members despite the variation in prosthetic diameter along its axis. Alternatively, the axially varying prostheses of the present invention comprise frame rings which vary in diameter with the liner, and therefore need not impose any internal stresses.

Several alternative methods are provided herein for selectively varying the perimeter of a liner along its axial length. The graft perimeter may be varied by simply forming curved axial joints along the prosthesis, typically by sewing a fabric graft, and optionally removing any excess material. However, graft liners are typically woven as continuous tubes. It is preferable to avoid any additional joints along a graft to minimize the danger of failure or leakage.

One advantageous method for axially varying the cross-section of a prosthesis is selectively shrinking the graft material. Grafts are often woven from synthetic fibers, typically comprising a polyester such as Dacron™. Such woven polyester liner tubes shrink when subjected to heat and/or certain chemicals. In particular, linear shrinkage of over 15% has been achieved using a 3–10% hexofluoro 2-propanol, 90–97% methylene chloride solution bath for a time between 2 and 30 minutes. Additionally, shrinkage of polyester and other synthetic graft materials is enhanced, or may be directly produced, by selective heating. Heating alone has produced up to 6% shrinkage, and it is anticipated that a combined heat/chemical process would provide 20% shrinkage. Grafts used in the axially variable prostheses of the present invention will preferably be initially woven as constant perimeter tubes, and will typically be shrunk at a selected cross-section by up to 18%.

Figure 7:
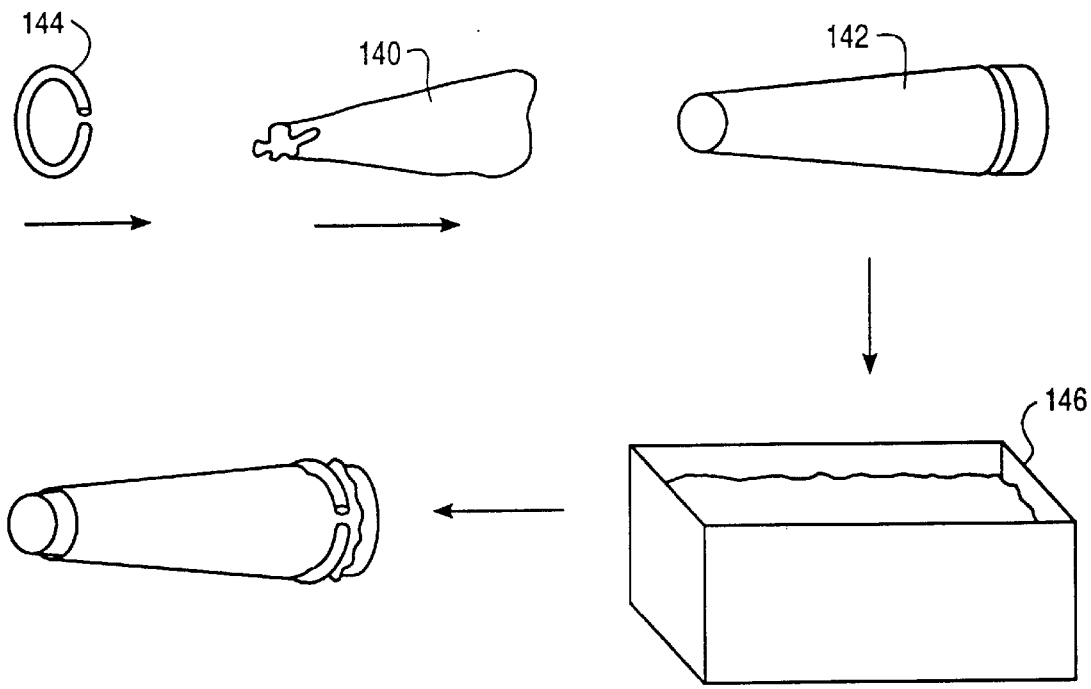
FIG. 7 illustrates a method for selectively shrinking a liner by restraining the liner on a mandrel and subjecting the restrained liner to a chemical bath, according to a method of the present invention.

Advantageously, precise control over the selective shrinking process may be obtained using a mandrel. Referring now to FIG. 7, cylindrical liner 140 slides over a tapered mandrel 142 and is held in place by a clip 144. The assembly is then placed in a chemical shrinking bath, as described above. The liner shrinks to precisely match the contour of tapered mandrel 142. The liner may then be removed and washed. The frame is generally attached to the liner after the liner has assumed its desired shape. Alternatively, an external mandrel may allow shrinking of an assembled liner-restrained stent-graft assembly, with an optional internal mandrel if the shrinking force is sufficient to overcome the expansive force of the frame.

Figure 7A:
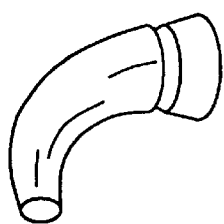
FIGS. 7A and 7B illustrate alternative mandrels for selectively shrinking liners to form bent and corrugated shapes, respectively, for use in the method of FIG. 7.
Figure 7B:
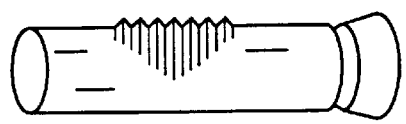
Figure 8A:
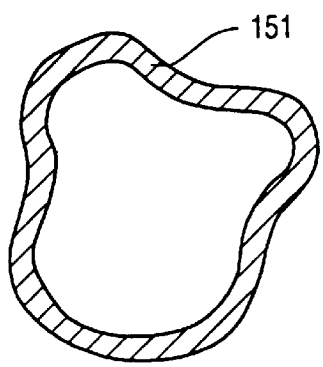
FIGS. 8A–D are cross-sections illustrating a method for plastically expanding a stent-graft having an expansible liner and a resilient frame, wherein the expanded stent-graft resiliently conforms to the irregular luminal wall.
Figure 8B:
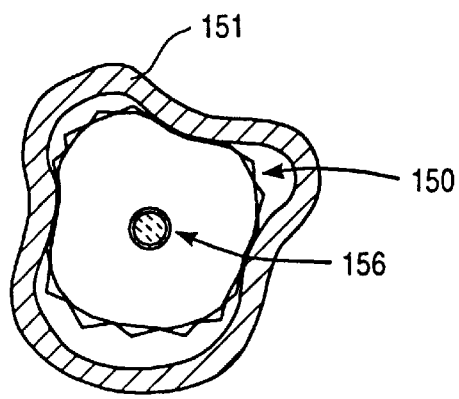
Figure 8C:
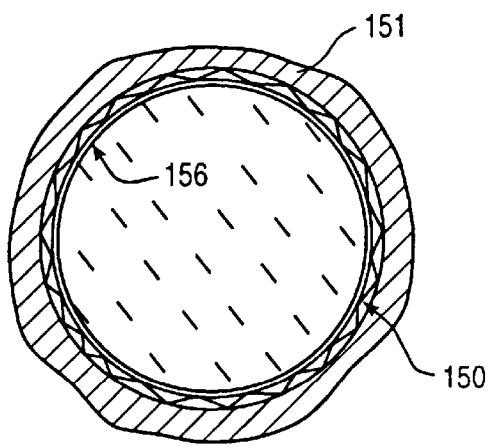
Figure 8D:
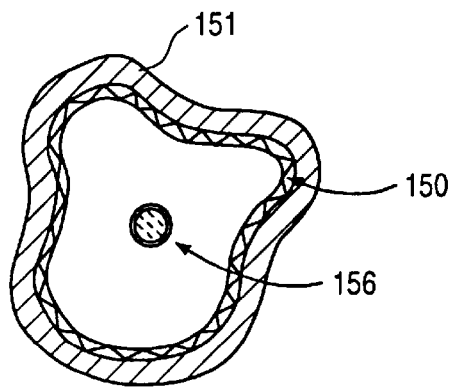

Referring now to FIGS. 7A and 7B, wide variety of mandrel shapes might be used to produce desired prostheses shapes. A curved mandrel 141 or a similar bent mandrel would allow production of specialized prosthetic shapes having a preset bend angle. A partially corrugated mandrel 143 provides axial flexibility, here allowing axial bending. The corrugation may be imposed over part or all of the liner. Complex mandrels may require internal joints to allow removal of the shaped, inelastic liner.

Figure 8:
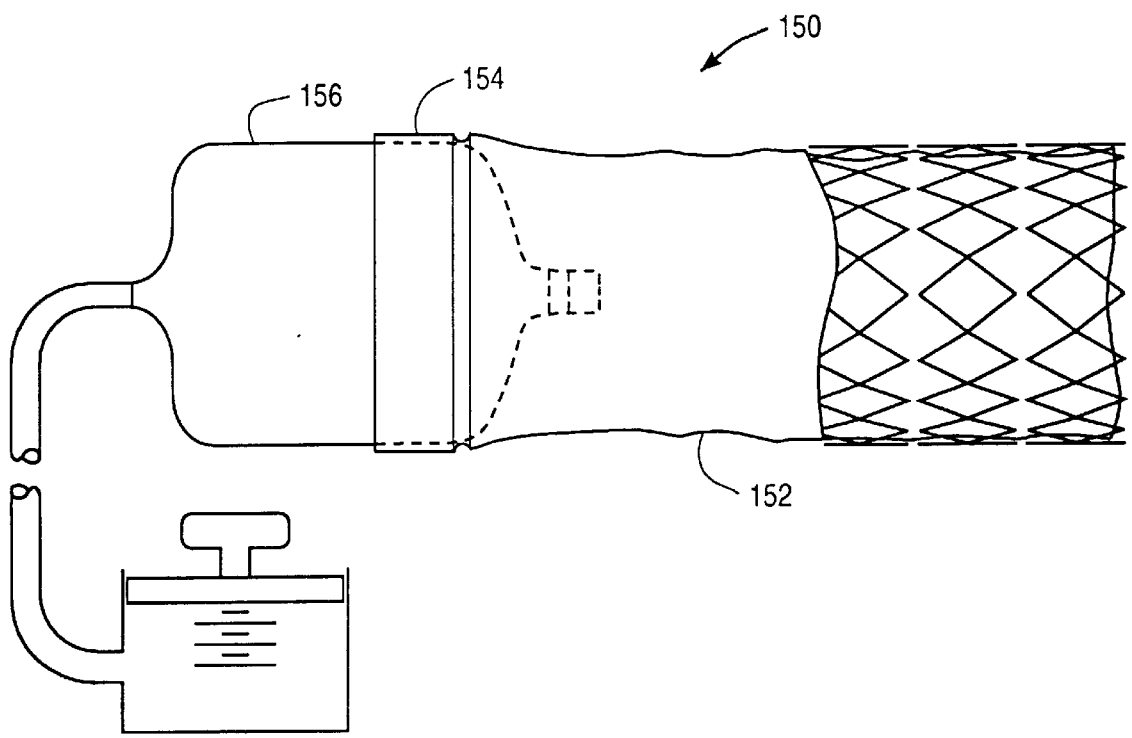
FIG. 8 illustrates a method for plastically expanding an expansible liner to axially vary the liner perimeter according to the principles of the present invention, wherein a portion of the outer frame has been removed for clarity.

Referring now to FIG. 8, an alternative method for forming a prosthesis having a varying cross-section comprises plastically expanding selected portions of an expansible prosthesis 150. Expansible prosthesis 150 is formed from radially compressible frame rings 112 and an expansible liner 152. Expansible liner 152 is formed from a material which expands plastically when subjected to a stress beyond a yield strength, and which remains expanded when the stress is removed, ideally exhibiting little or no spring back. By subjecting an enlargement portion 154 to the expansive force of balloon 156, the liner perimeter at a selected cross-section may be increased.

Advantageously, the varying cross-section of expansible prosthesis 150 may be imposed by selectively expanding expansible liner 152 prior to shipping the prosthesis as a production step, at the surgical site prior to introduction of the prosthesis within the patient body, or preferably after deployment of the prosthesis within a body lumen using an angioplasty-type balloon catheter or other expanding device.

Frame rings 112 of expansible prosthesis 150 may comprise a material which is resilient, malleable, or some combination of the two. When used with a resilient frame, frame rings 112 will generally be radially restrained by expansive liner 152 prior to plastic expansion of the prosthesis. Additionally, each stent ring 112 will preferably have a larger relaxed diameter than the associated section of expansible liner 152 after expansion. This avoids any lose fabric after balloon 156 has been removed, which would otherwise result from expansion of a liner to a greater perimeter than the frame.

The in situ expansion of expansible prosthesis 150 will be explained with reference to FIGS. 8A–D. Luminal wall 151 has the irregular cross-section shown upstream from an aneurysm. Prosthesis 150 expands resiliently within the luminal wall per FIG. 8B, but further expansion adjacent to the aneurysm might risk rupture. The balloon catheter 156 locally expands the liner of expansible prosthesis 150 without affecting the aneurysm, temporarily distending luminal wall 151. In contrast to a malleable prosthesis, which would retain the circular cross-section of the inflated balloon, expansible prosthesis 150 retains only the expanded perimeter and resiliently conforms to the luminal cross-section. Minimization of any spring-back in the liner also minimizes the temporary distention of luminal wall 151, while the liner-limited frame promotes sealing about the final perimeter.

Alternatively, plastic expansion of an expansive liner 152 is also advantageous when deploying a prosthesis having one or more frame rings 112 which comprise a malleable material. Such malleable prostheses are typically deployed using balloon catheter delivery systems, and an expansible liner provides a match between the expanded frame diameter and liner perimeter. The combination of one or more malleable frame rings and an expansible liner is particularly well suited for sealing the proximal and/or distal ends of endoluminal prostheses against the lumen wall, but does impose a circular cross-section on the luminal wall.

The total amount of expansion which can be imposed on expansible prosthesis 150 is largely dependent on the material selected for expansible liner 152. Grafts have generally been formed from fabrics and materials which are substantially impermeable to ensure that no leakage will occur through the liner. Such impermeable liner materials have tended to be either inelastic, as in the case of woven Dacron™, or susceptible to tearing, particularly at frame attachment points, as is the case for PTFE. By instead using an inelastic, plastically expandable graft material for expansible liner 152, expansible prosthesis 150 may be selectably expandable by as much as 80%, preferably being expandable by between 15% and 50%.

Figure 9A:
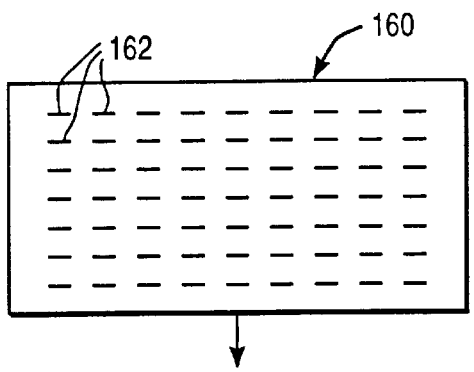
FIGS. 9A–C illustrate alternative expansible liner materials for use in the method of FIG. 8.
Figure 9B:
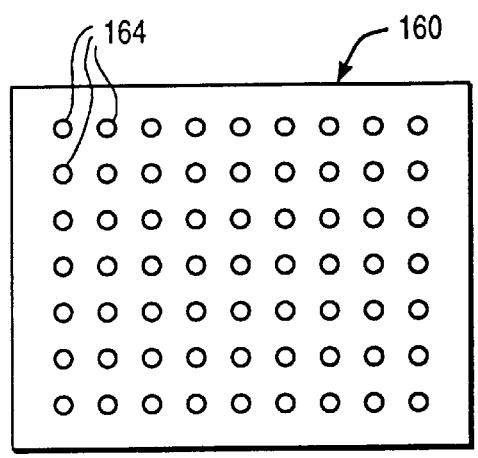

Referring now to FIGS. 9A and 9B, a first expansible material for use in expansible liner 152 (see FIG. 8) comprises a yieldable material 160 is formed from a fabric sheet having a large number of axial slits 162. The material preferably comprises a woven polyester, similar to impermeable liners, prior to cutting axial slits 162. Yieldable material 160 stretches when subjected to a radially expansive stress, in part by distorting the slits into holes 164. The size and spacing of the slits should thus be carefully selected to retain semi-permeable characteristics, i.e., to avoid hyperplastic ingrowth through the holes. Advantageously, a yieldable material offers a smooth surface when expanded, and requires a smaller amount of cloth volume to cover the same surface area as compared to impermeable materials, thereby allowing the size of the radially compressed prosthesis to be minimized.

When using yieldable material 160, sealing of the body lumen takes place due to coagulation of any blood which does seep through holes 164, while ingrowth of the body lumen wall into the stent-graft reduces stress on the weakened portion of the lumen wall. Yieldable expansible material 160 may be expanded by as much as 80%, which has advantages for any intraluminal prosthesis which must be radially compressed to the minimal possible diameter for introduction. However, expansion of such magnitudes typically results in a substantial increase in porosity.

Figure 9C:
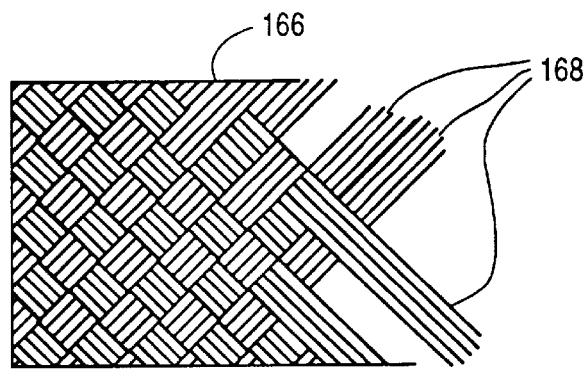
Figure 9D:
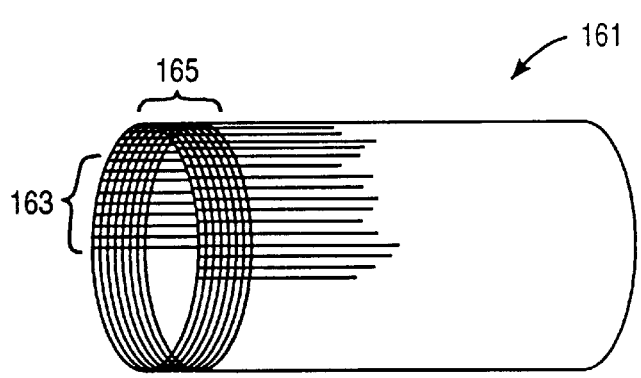
FIG. 9D illustrates a liner formed as a continuous woven tube for use in the endoluminal prostheses of the present invention.

A further alternative expansible material for use in the prosthesis of the present invention comprises a material which is braided, preferably from discrete strips of a woven fabric. Ideally, the woven fabric comprises a woven polyester such as Dacron. Referring now to FIG. 9C, braided graft 166 is braided from strips 168 in the shape of a tube. Braided graft 166 will expand outward easily, but outward expansion will be coupled with a decrease in length. The flexibility of stent-graft comprising braided graft will thus depend substantially on the frame, and on the frame/liner attachments in the case of a stent-graft having independent stent rings. One particularly advantageous method of attaching braided graft 166 to such independent stent rings comprises adhesive bonding.

A particularly advantageous alternative expansible material comprises a fabric produced from partially oriented fibers or yarns. Traditionally, textile grafts made for vascular use have been woven from yarns that were fully drawn, in other words, yarns in which substantially all of the fibers were fully axially oriented along the length of the yarn. Such fully oriented yarns prevent lose fabric caused by expansion of the graft material from interfering with flow through the lumen of the prosthesis. However, it has become increasingly important to reduce the size of invasive surgical devices and delivering apparatus so as to reduce incision sizes, and thereby promote patient healing and recovery. Accordingly, it has become advantageous to utilize materials that may be expanded after being delivered within the body.

A woven intraluminal liner 161 comprises a continuous tube having axially-oriented polyester fibers 163 and circumferentially-oriented fibers 165. Ideally the axially-oriented fibers, referred to as the "warp," comprise between 130 and 200 fibers per inch (sometimes called the "number of ends"). The circumferential fibers, called the "weave" or "fill," typically comprise between 60 and 100 fibers per inch. Selective use of partially oriented yarn for at least a portion of the circumferential or axial fibers of woven liner 161 provides a material which is expansible, samples of which have been expanded by up to 50% in diameter with a pressure of 35 PSI. Expansion by up to 80% or more is possible, although a substantial increase in porosity has been measured for partially oriented yarn fabric which has been expanded by over about 40%.

In connection with the present invention, it has been discovered that textile liners produced from partially oriented yarns may be expanded to effectively cover a larger area of a lumen wall than an equivalent volume of a textile graft made from the fully oriented yarns of the prior art. The expansible textile graft material of the present invention is typically woven from yarns having fibers which are only partially oriented, preferably being drawn to a length between 1% and 80% of their fully drawn length. Partially oriented yarn may also be formed by treating fully oriented yarns, i.e., fully drawn yarn may be twisted and then heat-set, shortening the length of the yarn prior to weaving fabric to provide the partially oriented effect.

Partially oriented yarn may be incorporated into a woven graft in either the circumferential orientation, the axial orientation, or both, depending on the desired expansion properties. Ideally, partially oriented yarns are primarily used in the circumferential orientation. This facilitates radial expansion of the completed endoluminal prosthesis, without producing excessive amounts of axial elongation or hysteresis during use.

It will be recognized that the expansible partially oriented yarn textile of the present invention also provides significant advantages over such polymeric materials as PTFE. Specifically, PTFE is susceptible to tearing when sutured or pierced by mechanical attachments. Additionally, partially oriented yarns of the present invention may be formed from polyester fibers. These fibers are available from a wide number of sources, and can be processed using inexpensive and widely available textile machinery.

Figure 9E:
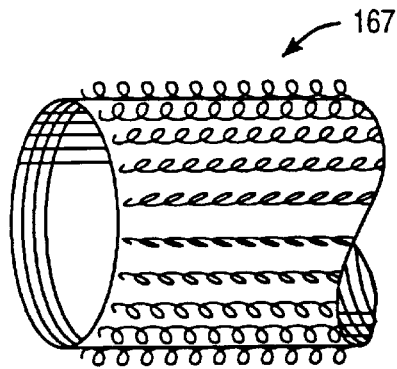
FIG. 9E illustrates a liner having radially protruding fibers to promote ingrowth, sealing, and/or coagulation over the outer surface of the prostheses of the present invention.

A still further alternative expansible material according to the present invention comprises a knitted material. Knitted materials are easily made expansible because of the loops formed in their fibers. Clearly, partially oriented yarn could be knit to form a highly expansible material. Such a knitted material, or any textile liner, may also be formed as a fuzzy liner 167 as shown in FIG. 9E. Fuzzy liner 167 comprises protruding fibers or fiber loops which extend radially outward. Such fibers should improve the peripheral seal between the liner and an adjacent luminal wall, and may promote coagulation of any blood which leaks around the tubular prosthesis. Furthermore, the fibers may promote ingrowth of tissue to permanently anchor the prosthesis, and without intruding into the relatively smooth inner lumen of the prosthesis.

Liner Attachment

Stent-grafts and other endoluminal prostheses often include a plurality of independent liner frame elements attached to a liner. The flexing characteristics of such prostheses will be determined in part by the size and shape of the frame, and in part by the properties of the liner material. Additionally, the flexing characteristics of stent-grafts in general have been found to be highly dependent on the specific method used to attach the frame to the liner.

Figure 10B:
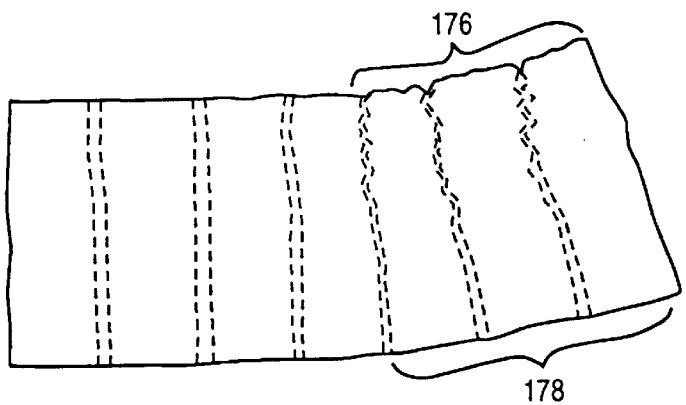
FIG. 10B illustrates the liner of the stent-graft of FIG. 10A with the frame removed for clarity.
Figure 10A:
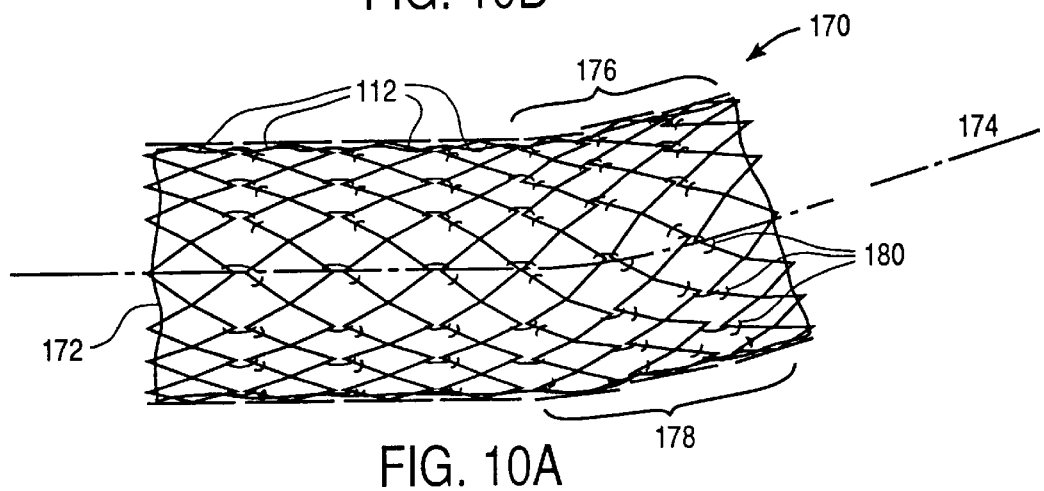
FIG. 10A illustrates a stent-graft wherein the stent comprises individual frame rings which are attached by threads that allow a controlled amount of flexibility, according to the principles of the present invention.

Referring now to FIG. 10A, a stent-graft 170 comprises a plurality of individual frame rings 112 attached to an inner liner 172. When stent-graft 170 is flexed about its axis 174, the frames on an inner bend region 176 are brought together, often overlapping under a local compressive force. Meanwhile, the frames on an outer bend region 178 are spread out by a similar local tensile force. These compressive and tensile force are transmitted between frame rings 112 by inner liner 172. Frame rings 112, in turn, transmit these forces to and from the liner through sewn threads 180.

Referring now the FIG. 10B, bending imposes tensile and compressive forces on inner liner 172, which is shown with frame rings 112 removed for clarity. Inner bend region 176 can be seen to be wrinkled, which reduces the effective cross-sectional size of the central lumen. The size and characteristics of the wrinkles depend on how far frame rings 112 have been displaced from a nominal straight position, and also on the location of the attaching threads 180. Further bending may impose an inward kink in the liner, causing a dramatic decrease in any flow through the prosthesis. Outer bend region 178 remains relatively smooth, as the material is held in position and under tension by the frames through threads 180 (see FIG. 10A).

The frame to liner attachment can serve multiple purposes. First, the attachments hold the liner in an open configuration, minimizing wrinkles and discontinuities of the inner lumen which would otherwise reduce luminal flow. Second, the attachments can provide a mode for stent-graft flexibility by allowing some relative movement between adjacent frame elements. Third, the attachments will provide column strength to the prosthesis, with increasing column strength often requiring some trade-off with regard to flexibility. Fourth, the attachment can be used to vary the flexibility of the along or within the prosthesis. Fifth, the location of attachments on the frame may promote or inhibit protrusion of frame structure to act as interface barbs, as described above.

Figure 11A:
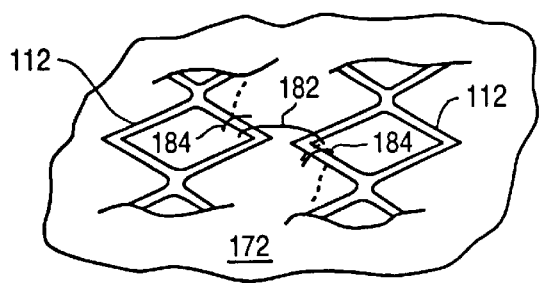
FIGS. 11A and 11B illustrate a preferred stitching pattern which provides a controlled amount of flexibility in the stent-graft of FIG. 10A.
Figure 11B:
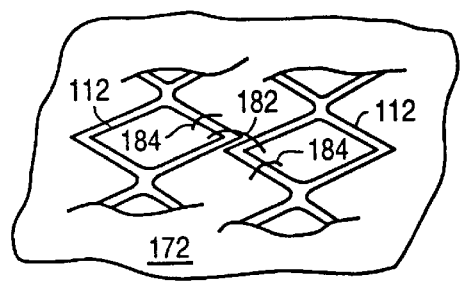

Referring now to FIGS. 11A–B, a preferred sliding thread pattern for attaching frame rings 112 to inner liner 172 comprises an interframe loop 182 passing around both frames and a slider loop which passes around one arm of each frame ring 112. Interframe loop 182 limits to distance between the frames under tension, as seen in FIG. 11A.

Optionally, multiple interframe loops may be included for high tension loads. Slider loops 184 allow the frames to slide toward each other over the surface of inner liner 172 without any wrinkling of the liner for a limited distance, but will restrict movement beyond that limit, as seen in FIG. 11B. The actual sliding limit size is determined by the amount of liner material encompassed by slider loops 172.

Figure 11C:
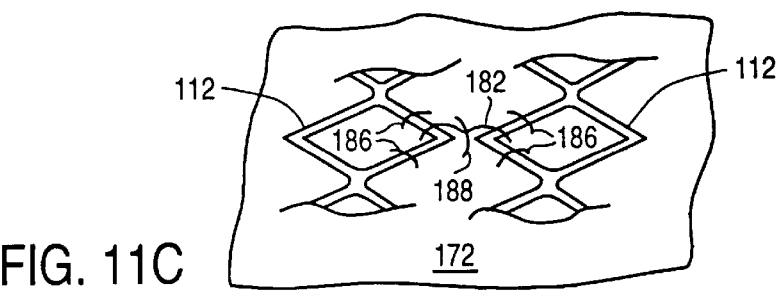
FIG. 11C illustrates a stitching pattern which locks the frame rings to each other, thereby allowing variations in flexibility when used in the stent-graft of FIG. 10A.

An alternative locking thread pattern illustrated in FIG. 11C will directly transfer any compressive or tensile forces between the frames. Arm loops 186 encompass each of the two arms of the frame, while interframe loop 182 again encompasses both frame rings 112, here encircled by a cross loop 188. This stitching pattern effectively "locks" the frames together, substantially eliminating any overlapping or separation of the frames. Care must be taken in placing such stitches on opposite sides of a ring frame to ensure that the frame is free to radially compress, as the diamond elements expand axially during compression.

Selective use of such locking stitch patterns, as shown in FIG. 11C, with the sliding stitch pattern, as shown in FIGS. 11A–B, allows a variation in flexibility over an otherwise uniform stent-graft. Flexibility can vary along the axis of the stent-graft by use of different stitch patterns along the prosthesis axis. Alternatively, to facilitate bending of the prosthesis about its axis in one orientation, use of a locking pattern at a preferred outer bend region will prevent overlap, while a sliding pattern at an opposed inner bend region will promote overlap within a limited orientation.

Figure 12C:
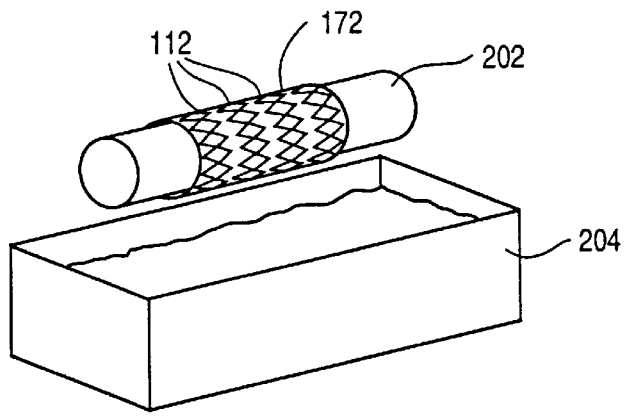
FIGS. 12A–F illustrate alternative stent/graft attachment methods for use in the stent-graft of FIG. 10A.
Figure 12A:
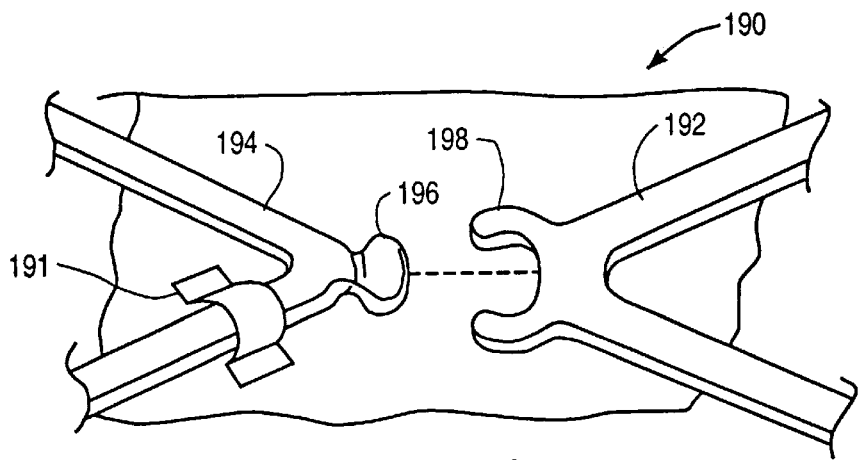
Figure 12B:
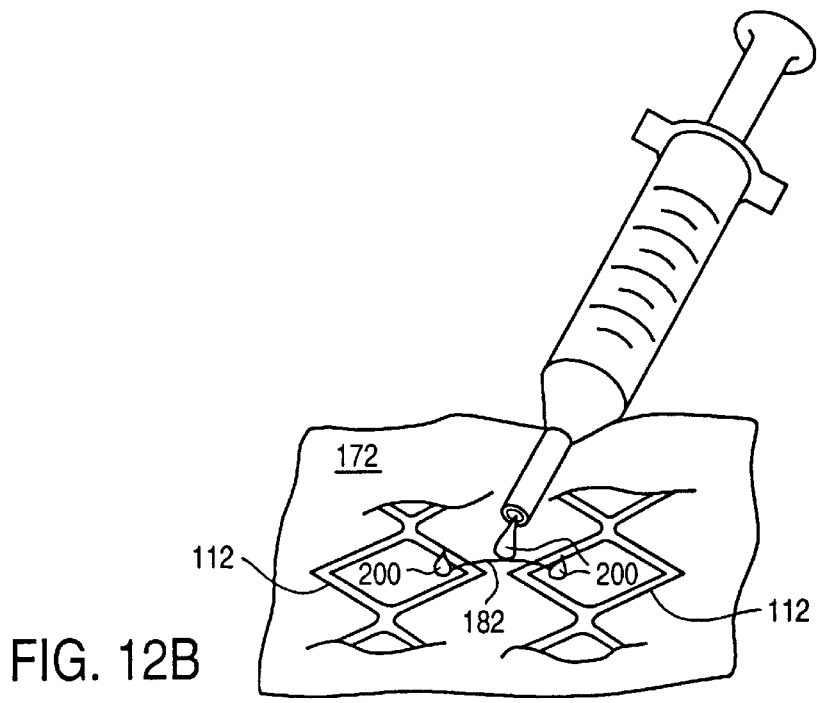

FIGS. 12A–C illustrate alternative liner/frame attachments. In FIG. 12A, a clip 190 between adjacent frames 192, 194 comprises a ball 196 and a socket 198. Optionally, ball 196 clips into socket 196 to limit relative movement between the frames, acting as a ball and socket joint. Alternatively, ball 196 slides within an elongated socket to provide a controlled amount of translation of the frames. In some embodiments, clip 190 may facilitate attachment of the liner by inserting a tab of liner material between the ball and socket, and attaching the tab to the liner. A staple 191 is shown attaching the frame to the liner, which staple may include barbs piercing the liner material and then bent over, or may simply be sewn into place. FIG. 12B illustrates the use of an adhesive 200 together with a sewn attachment pattern to enhance the liner/frame attachment. Suitable adhesives include silicone elastomer, Loctite™ and other cyanoacrylates, and the like. Alternatively, a polyester solvent may be used to "weld" a polyester liner to polyester threads.

FIG. 12C illustrates a method for attaching a liner to a prosthesis frame which comprises assembling the liner 172 and ring fames 112 on a mandrel 202. Mandrel 202 typically includes a low friction coating, such as PTFE or the like. The entire assembly is then coated with a thin layer of a tough silicone dispersion within the coating bath. The silicone coated frame and liner are then removed from the mandrel, avoiding the time consuming process of individually stitching the fames. Alternatively, the dispersion comprises a polyester in a suitable solvent, such as a solution of hexofluoro 2-propanol and methylene chloride.

Figure 12D:
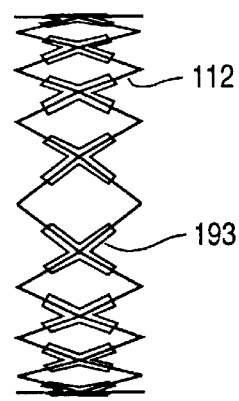
Figure 12E:
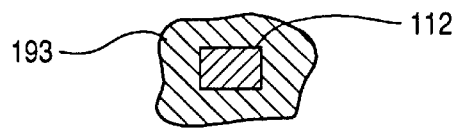
Figure 12F:
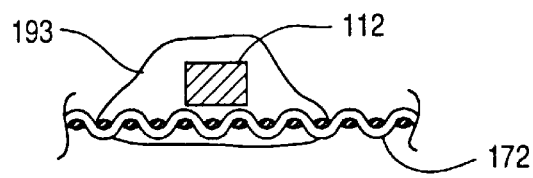

A method for selectively powdercoat bonding a frame to a liner will be described with reference to FIGS. 12D–F. Very fine particles of a suitable adhesive, typically comprising a polyester resin, will adhere electrostatically when sprayed on ring frame 112. The particles may optionally be masked or removed to form a selective coating 193. The selective coating 193 may be partially cured on the frame to facilitate handling and allow positioning of the liner relative to the frame. The liner, frame, and partially cured powdercoat are bonded by heating, the selective coating 193 melting so that the powdercoat polymer material encompasses the liner adjacent to the frame.

Figure 13A:
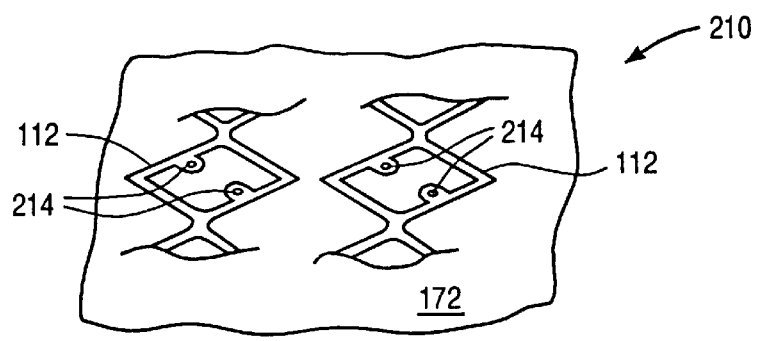
FIGS. 13A–C illustrate an alternative stent/graft attachment rivet and an alternative tabbed ring stent, both for use in the stent-graft of FIG. 10A.
Figure 13B:
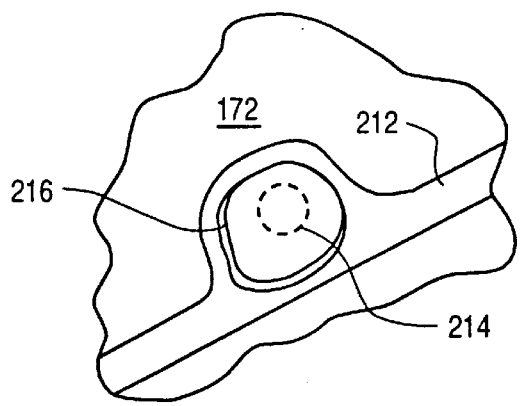
Figure 13C:
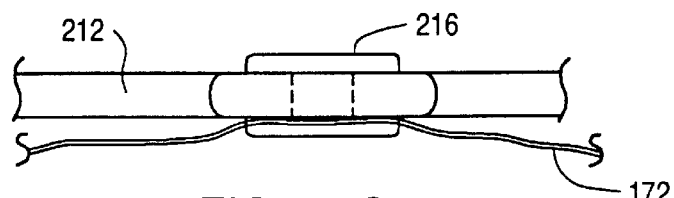

A mechanical "rivet" frame/liner attachment 210 will be described with reference to FIGS. 13A–C. Tabbed frames 212 include attachment holes 214. Extending through each attachment hole 172 is a hardened polyester rivet 216. The liner is disposed within the inner enlarged portion of the rivet, which is formed from liquid polyester or the like. Ideally, the rivets "wick" completely through a textile liner without weakening the liner by cutting threads. Alternatively, attachment holes 172 may be used to sew the frame to the liner.

Figure 14A:
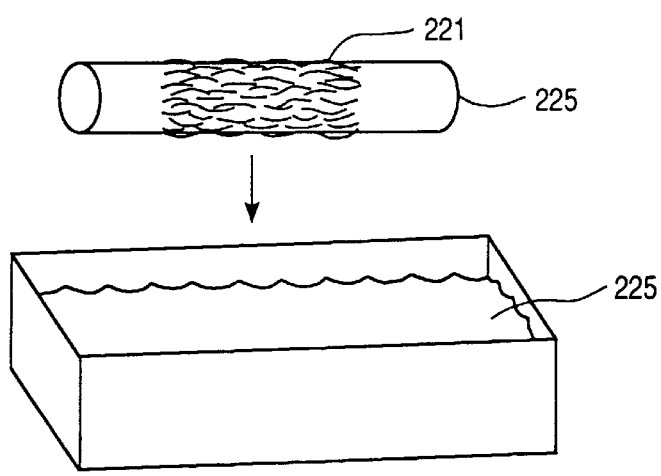
FIGS. 14A–C illustrate a braid reinforced elastomeric prosthesis and a method for its production, according to the principles of the present invention.
Figure 14:
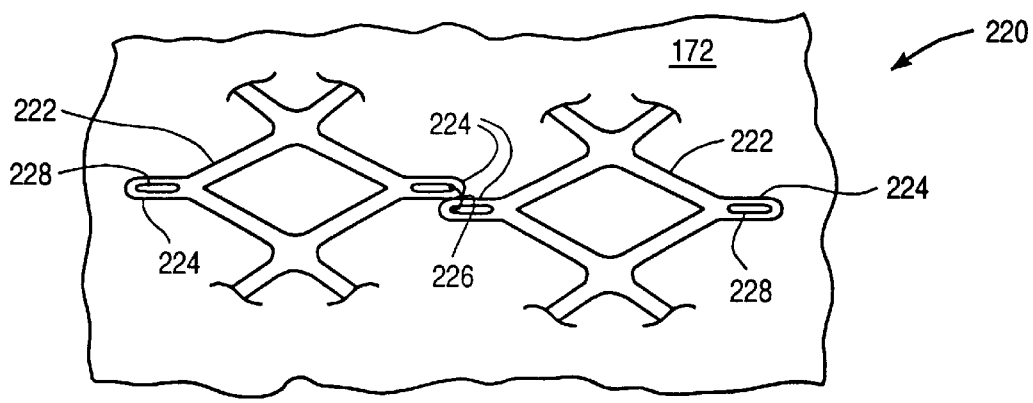
FIG. 14 illustrates a preferred slotted stent ring which provides precise and variable control over the flexibility of the stent-graft of FIG. 10A.

Referring now to FIG. 14, a particularly advantageous liner/frame slot attachment 220 utilizes slotted frames 222 having slot tabs 224 which preferably extend axially from the frames. The liner 172 is sewn with a slot loop which extends through slots 228 of both adjacent frames. The movement of the frames relative to liner 172 is thus controlled by the length of the individual slots, while the relative movement between the frames is controlled by the total combined slot length of the two attached slots. Conveniently, the slot length may be varied axially and circumferentially, allowing axial and orientation-dependent variations in prosthesis flexibility as described above. For example, a slotted frame could be sutured directly to a hole in a tabbed frame (see FIGS. 13A–C) or to a liner adjacent to a ring frame. Optionally, frames which are directly sutured, riveted, or otherwise directly connected using such slots could be used without a liner as a stent. Alternatively, a liner could be attached by some separate mechanism, such as powdercoat bonding (see FIGS. 12D–F).

Figure 14B:
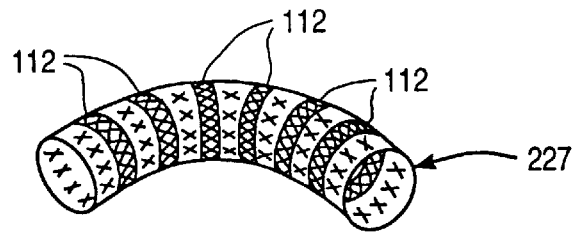
Figure 14C:
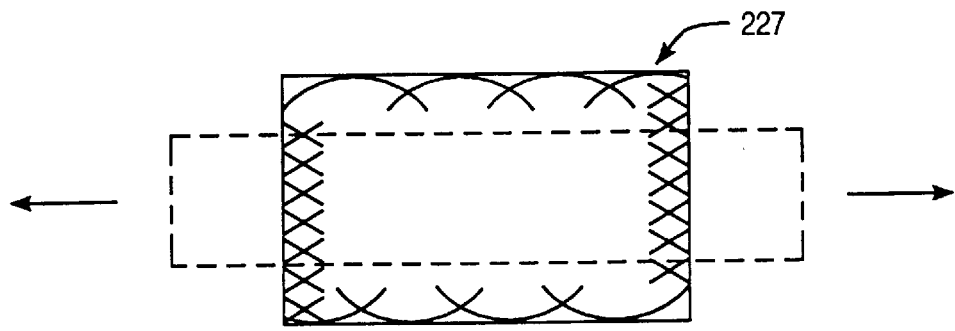

Referring now to FIGS. 14A–C, a kink-resistant prosthesis 227 utilizes a braid-reinforced elastomer to provide axial flexibility without the wrinkling or folding seen in the inelastic liner of FIG. 10B. Braided polymer tubes alone are highly flexible structures which bend without wrinkling, but lack the structural integrity desired for intraluminal prosthesis. A braided polymer tube 221, typically comprising braided polyester elements such as Dacron™, is placed on a mandrel 223 typically having PTFE or a mold release over its surface. The mandrel and braid are immersed or otherwise coated with a curable elastomer 225, typically being silicone, urethane, or rubber, the elastomer capable of being oven-cured. Ideally, the braid-reinforced elastomer is supported by a plurality of independent ring frames 112, which may be bonded in place or positioned on the mandrel with the braid.

The resulting kink-resistant prosthesis 227 will maintain a patent lumen surface during axial bending through the interaction of the braid and ring frame structures. The elastomer provides a smooth, flexible sealing surface, as well as the desired prosthetic structural integrity. The kink-resistant prosthesis will also be radially compressible, but the diameter and length are closely coupled, specifically being inversely proportional as shown in FIG. 14C.

Figure 14D:
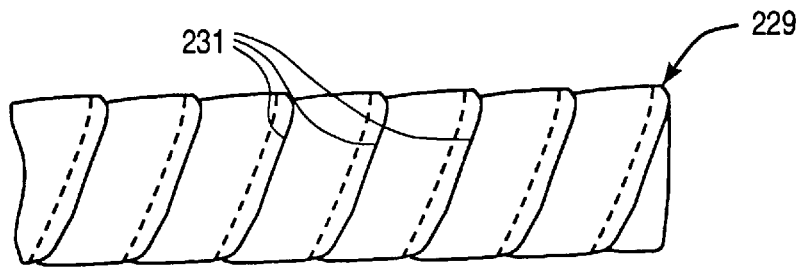
FIGS. 14D–E illustrate alternative liner structures permitting axial flexure.
Figure 14E:
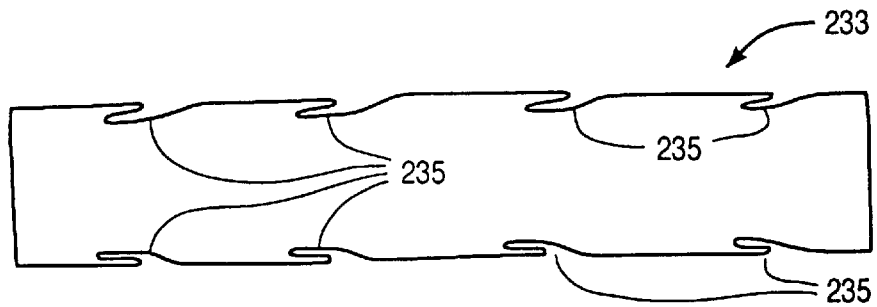

Referring now to FIGS. 14D and 14E, local or total prosthesis elongation may be provided by a spiral liner 229 having a spiral overlap 231, or by an eversed liner 233 having one or more circumferential eversed sections. Additionally, a corrugated liner, optionally formed over a fully or partially corrugated mandrel similar to that shown in FIG. 7B, would allow both elongation and compression from a relaxed position.

Sealing/Anchoring Cuffs

Figure 15:
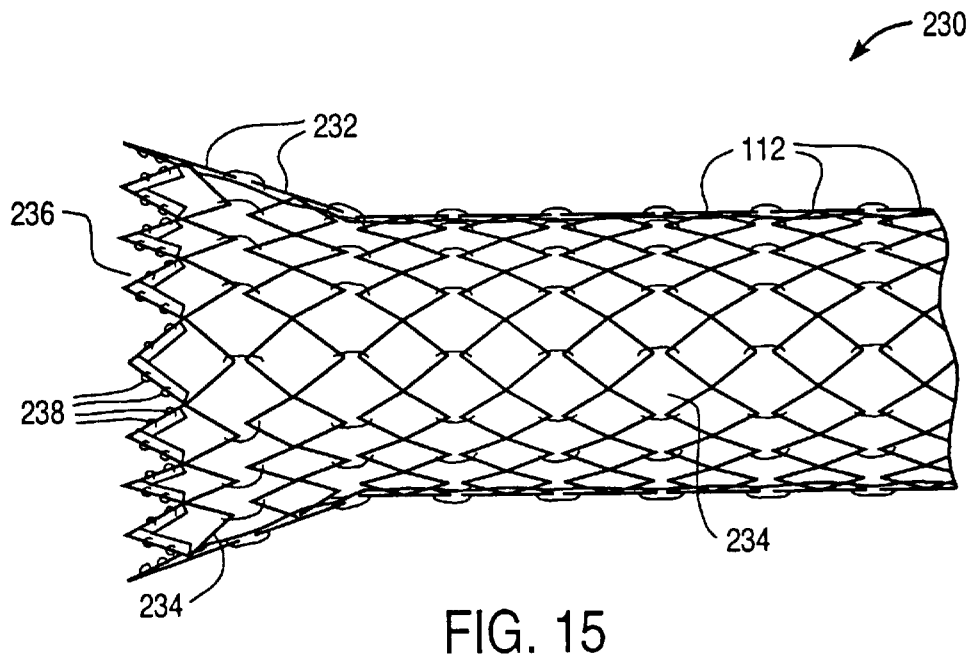
FIG. 15 illustrates a flared expansile cuff for anchoring and sealing the end of the prosthesis against the body lumen, according to the principles of the present invention.

As described briefly above, a particularly advantageous use for the axial variation in prosthetic characteristics of the present invention is to provide a flared end on a prosthesis which anchors the prosthesis and seals the end of the prosthesis against the body lumen wall. Referring now to FIG. 15, a cuffed prosthesis 230 comprises a plurality of flared stent rings 232 and a flared liner 234, both of which have an increased cross-section at a flared end 232. Flared stent rings 232 optionally comprise liner restrained uniform resilient frame rings 112 which flared liner 234 allows to expand to a relatively large diameter.

The liner is folded over so as to cover and seal against the extreme furthest structure of flared end 236, which is the outermost portion of the frame, and is sewn in position by crown threads 238. Advantageously, this minimizes any leakage between the prosthesis and the lumen wall. To further reduce leakage and improve anchoring, the flared stent rings optionally expand with increased resilient force. Cuffed prosthesis 230 ideally includes two flared ends to seal and anchor the prosthesis both distally and proximally of the weakened blood vessel wall associated with an aneurysm.

Figures 16A, 16B:
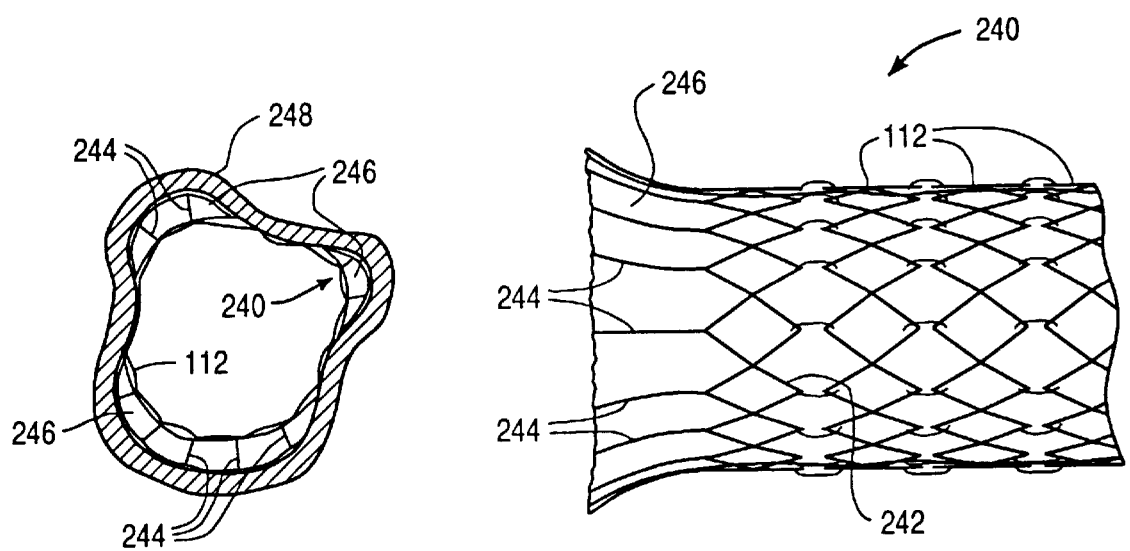
FIG. 16A illustrates an endoluminal prosthesis having a conformal expansile cuff formed from resilient frame extensions and a flexible liner material, according to the principles of the present invention.
FIG. 16B illustrates the endoluminal prosthesis of FIG. 16A positioned in an irregular body lumen, the cuff conforming to the irregular cross-section to seal the end of the prosthesis against the lumen wall.

Referring now to FIGS. 16A and B, a conformal cuffed prosthesis 240 comprises an extension stent ring 242 having resilient extensions 244, which are highly flexible and resilient, typically comprising a shape memory alloy such as Nitinol™. A conformal liner 246 is spread open by extensions 244, and comprises a flexible material. When conformal cuffed prosthesis 240 is placed in an irregular body lumen 248, frame rings 112 resiliently expand against the lumen wall, but do not seal around the entire perimeter. However, extensions 244 spread conformal liner outward 246 to more fully seal the end of conformal cuffed prosthesis 240 around the perimeter of irregular body lumen 248.

Finally, it will be recognized that the "fuzzy" liner of FIG. 9E is particularly advantageous for sealing and anchoring adjacent to and/or on the cuffs of cuffed prostheses 230, 240.

Spring Force Variations

It is often advantageous to vary the spring force within a resilient prosthesis. For example, referring once again to FIG. 15, flared stent rings 232 of flared prosthesis 230 substantially form both the anchor and the seal between the prosthesis and the body lumen wall. These two different functions, sealing and anchoring, represent conflicting criteria from selecting the resilient expansive spring force of the frame in a resilient stent-graft. The present invention overcomes this conflict by providing a relatively stiff portion of the frame having a high radially-expansive spring force relative to a conformable portion of the frame.

Where the frame comprises a plurality of independent ring frames, the ring frame material or thickness can be varied axially by selective use of differing ring frames. However, this may increase production costs by increasing the number of different parts which must be fabricated for each prosthesis. Where the ring frames comprise a shape-memory alloy, such as Nitinol™ or the like, the spring force or otherwise similar ring frames can be varied by imposing different heat treatments. Thus, different radial spring forces can be provided along the axis of the prosthesis without separately cutting and forming different ring frames.

Heat treatments may vary radial spring force by varying Af, the Austenite finish transformation temperature. Lower Af temperatures generally produce structures which are superelastic, and therefore stiffer, at certain temperatures. Additionally, heat treatments of superelastic materials are used to establish the "relaxed" shape at different temperature ranges. Heat treating the ring frames for different relaxed sizes at body temperature will thus impose different spring forces, even though the frames are restrained at the same diameter (i.e., within a body lumen or a liner-limited stent-graft). Clearly, spring force variation may alternatively be achieved by varying frame thickness, by selectively machining the ring frames, by using different alloys, or the like.

As can be understood with reference to FIGS. 15–16B, the sealing portion of an expansile cuff may optionally comprises a structure having a higher radial spring force or a structure having a lower radial spring force. A higher spring force in flared ring frames 232 will force the surrounding vessel to conform to the shape of the cuff, at least to some extent. In contrast, a lower spring force, such as that provided by extensions 244, in combination with a conformable liner will result in an expansile cuff which more closely assumes the original shape of the vessel wall. Clearly, further combinations of frame and vessel conformance are also possible, depending on the radial stiffness of the frame, liner, and artery surface. As a further example, the final flared frame ring 232 adjacent the terminal end of flared prosthesis 230 might be low in stiffness to provide sealing, while the adjacent flared frame ring was stiff to provide an anchor, within the scope of the present invention.

Finally, it should be recognized that still further variations in radial spring force may be provided within a single frame structure by providing different heat treatments to different regions of the frame.

While the foregoing has been described in some detail, for purposes of clarity and understanding, certain changes and modifications will be obvious to those of skill in the art. Thus, the scope of the present invention is limited only by the appended claims.

What is claimed is:

1. A cuffed endoluminal prosthesis comprising:
   a radially expandable tubular body portion having a proximal end, a distal end, and a lumen therebetween;
   an expansile cuff module disposed on at least one of the proximal and distal ends, the cuff module expandable to sealingly engage a luminal wall of a body lumen having an inner perimeter greater than an outer perimeter of the expanded body portion.

2. A cuffed endoluminal prosthesis as claimed in claim 1, wherein the cuff module is radially flared outward relative to the body portion.

3. A cuffed endoluminal prosthesis comprising:
   a radially expandable tubular body portion having a proximal end, a distal end, and a lumen therebetween;
   an expansile cuff module disposed on at least one of the proximal and distal ends, the cuff expandable to sealingly engage a luminal wall of a body lumen having an inner perimeter greater than an outer perimeter of the expanded body portion,
   wherein the body expands resiliently and the cuff module has a higher expansive spring force than the body to conform the luminal wall to the cuff module.

4. A cuffed endoluminal prosthesis comprising:
   a radially expandable tubular body portion having a proximal end, a distal end, and a lumen therebetween;
   an expansile cuff module disposed on at least one of the proximal and distal ends, the cuff module expandable to sealingly engage a luminal wall of a body lumen having an inner perimeter greater than an outer perimeter of the expanded body portion,
   wherein the cuff module is more radially conformable than the body portion.

5. A cuffed endoluminal prosthesis as claimed in claim 1, wherein the cuff module comprises a cuff frame and a tubular cuff liner supported by the frame, the cuff liner extending axially and folding over an extreme end of the cuff frame.

6. A cuffed endoluminal prosthesis comprising:
a radially expandable tubular body portion having a proximal end, a distal end, and a lumen therebetween;
an expansile cuff module disposed on at least one of the proximal and distal ends, the cuff module expandable to sealingly engage a luminal wall of a body lumen having an inner perimeter greater than an outer perimeter of the expanded body portion;
wherein the cuff module comprises a member comprising a liner supported independent expansile ring frame.

* * * * *